United States Patent
Vincent et al.

(10) Patent No.: US 12,276,712 B2
(45) Date of Patent: Apr. 15, 2025

(54) SYSTEMS, ASSEMBLIES, AND METHODS OF FABRICATION OF LIQUID METAL RADIO-FREQUENCY COIL ASSEMBLIES OF A MAGNETIC RESONANCE SYSTEM

(71) Applicant: GE Precision Healthcare LLC, Wauwatosa, WI (US)

(72) Inventors: Jana M. Vincent, Aurora, OH (US); Fraser J. L. Robb, Aurora, OH (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 167 days.

(21) Appl. No.: 18/312,999

(22) Filed: May 5, 2023

(65) Prior Publication Data

US 2024/0369655 A1 Nov. 7, 2024

(51) Int. Cl.
*G01R 33/34* (2006.01)
*A61B 5/055* (2006.01)
*G01R 33/385* (2006.01)

(52) U.S. Cl.
CPC ........ *G01R 33/34092* (2013.01); *A61B 5/055* (2013.01); *G01R 33/34084* (2013.01); *G01R 33/385* (2013.01)

(58) Field of Classification Search
CPC ........ G01R 33/34092; G01R 33/34084; G01R 33/385; G01R 33/34007; A61B 5/055
See application file for complete search history.

(56) References Cited

U.S. PATENT DOCUMENTS

2022/0252684 A1 8/2022 Rispoli
2023/0368971 A1* 11/2023 Lu ................... H01F 41/043

FOREIGN PATENT DOCUMENTS

DE 102008051945 A1 * 5/2009 ............ D05B 29/06
EP 3889631 A1 * 10/2021

OTHER PUBLICATIONS

Machine translation of DE-102008051945-A1 (Year: 2009).*
"Applique Foot AP for Janome 9mm Machines", YouTube Video, dated Feb. 15, 2013, accessed online at URL: https://www.youtube.com/watchv=-QWE7HyAers.
(Continued)

Primary Examiner — G. M. A Hyder
(74) Attorney, Agent, or Firm — Armstrong Teasdale LLP

(57) ABSTRACT

A method of fabricating a liquid metal radio-frequency (RF) coil assembly of a magnetic resonance (MR) system using a sewing machine is provided. The method includes providing a sewing accessory assembly, the sewing accessory assembly including a substrate holder and a presser foot. The method also includes attaching the presser foot with a sewing machine, positioning the substrate holder containing a first substrate underneath a needle arm of the sewing machine, and carving a pattern of grooves on a surface of the first substrate using the presser foot by operating the sewing machine. The method further includes forming RF coil loops by depositing liquid metal in the grooves and applying a second substrate over the RF coil loops.

20 Claims, 20 Drawing Sheets

(56) References Cited

OTHER PUBLICATIONS

"Brother Universal Sewing Machine Needles (5 Piece)", Walmart Product Webpage, accessed online on Apr. 26, 2023 at URL: https://www.walmart.com/ip/Brother-Universal-Sewing-Machine-Needles-5-Piece/51741793wmlspartner=wlpa selectedSellerId=0 wl13=5313adid=2222222227751741793_117755028669_12420145346 wmlspartner=wmtlabs wl0= wl1=g wl2=cwl3=501107745824 wl4=pla-294505072980 wl5=9022943 wl6= wl7= wl8= wl9-pla wl10-8175035 wl11=localwl12=51741793 wl13=5313 veh=sem_LIA.

"Janome Applique Foot for 9mm Machines", Amazon Product Webpage, acessed online on Apr. 25, 2023 at URL: https://www.amazon.com/Janome-Applique-Foot-9mm-Machines/dp/B00MGVRD24/ref=asc_df_B00MGVRD24/tag=hyprod-20 linkCode=df0 hvadid=196246093157 hvpos= hvnetw=g hvrand=4056505097726588721 hvpone=hvptwo= hvqmt= hvdev=c hvdvcmdl= hvlocint= hvlocphy=9022943 hvtargid=pla-316024472388 psc=1.

"Round Bead Foot", YouTube Video, dated Oct. 30, 2021, accessed online at URL: https://www.youtube.com/watchv=xYs4cZaOh-c.

"Sew Tech Embroidery Hoops for Brother SE600 PE550D SE700 PE535 SE400 PE525 PE540D PE500 SE625 SE425 Innovis Babylock Brother Embroidery Machine Hoop (3in1 Set)", Amazon Product Webpage, accessed online on Apr. 26, 2023 at URL: https://www.amazon.com/Embroidery-Brother-Innovis-Babylock-Machine/dp/B07YVJ14K7/ref=asc_df_B07YVJ14K7/tag= linkCode=df0 hvadid=385122001650 hvpos= hvnetw=ghvrand=17704998920789097311 hvpone= hvptwo= hvqmt= hvdev=c hvdvcmdl= hvlocint= hvlocphy=9022943hvtargid=pla-833193096409 ref= adgrpid=78285594373 th=1.

"Singer Beading Foot", Joann Product Webpage, accessed online on Apr. 25, 2023 at URL: https://www.joann.com/singer-beading-foot/18429068.htmlgclid=EAlalQobChMircHUz4bF_gIVGQytBh34fQ-HEAQYASABEgKkZfD_BwE.

Agir et al., "A Wearable and Flexible 23Na Transmit/Receive Breast Coil at 3T", No. 4104, Proc. Intl. Soc. Mag. Reson. Med. 28 (2020).

Corea et al., "Screen-printed flexible MRI receive coils", Nat Commun 7, 10839 (2016), published Mar. 10, 2016, DOI: https://doi.org/10.1038/ncomms10839.

Motovilova et al., "Stretchable self-tuning MRI receive coils based on liquid metal technology (LiquiTune)", Sci Rep 11, 16228 (2021), published Aug. 10, 2021, DOI: https://doi.org/10.1038/s41598-021-95335-6.

Nordmeyer-Massner et al., "MR imaging of healthy knees in varying degrees of flexion using a stretchable coil array provides comparable image quality compared to a standard knee coil array", Eur J Radiol, Mar. 2016;85(3):518-23, doi: 10.1016/j.ejrad.2015.12.004, Epub Dec. 18, 2015.

Port et al., "Detector clothes for Mri: A wearable array receiver based on liquid metal in elastic tubes", Sci Rep 10, 8844 (2020), published Jun. 1, 2020, DOI: https://doi.org/10.1038/s41598-020-65634-5.

Port et al., "Elastomer coils for wearable MR detection", vol. 85, Issue 5, May 2021, pp. 2882-2891, First published Jan. 12, 2021, DOI: https://doi.org/10.1002/mrm.28662.

Port et al., "Towards wearable MR detection: A stretchable wrist array with on-body digitization", No. 0017, Proc. Intl. Soc. Mag. Reson. Med. 26 (2018).

Varga et al., "Adsorbed Eutectic Galn Structures on a Neoprene Foam for Stretchable MRI Coils", Adv Mater. Nov. 2017;29(44), First published Oct. 13, 2017, doi: 10.1002/adma.201703744.

Vincent et al., "Twenty-channel, Highly-stretchable, Overlapped, Receive (THOR) Array", May 7-12, 2022, Joint Annual Meeting ISMRM-ESMRMB, ISMRT 31st Aannual Meeting.

* cited by examiner

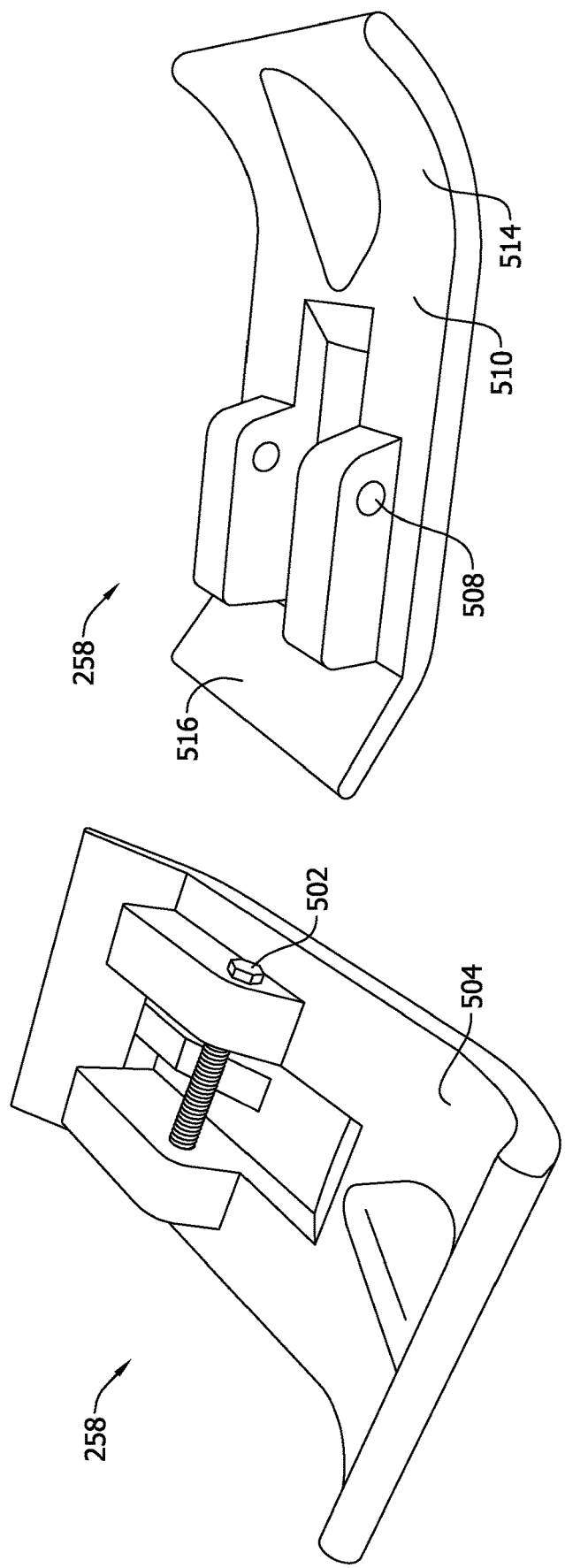

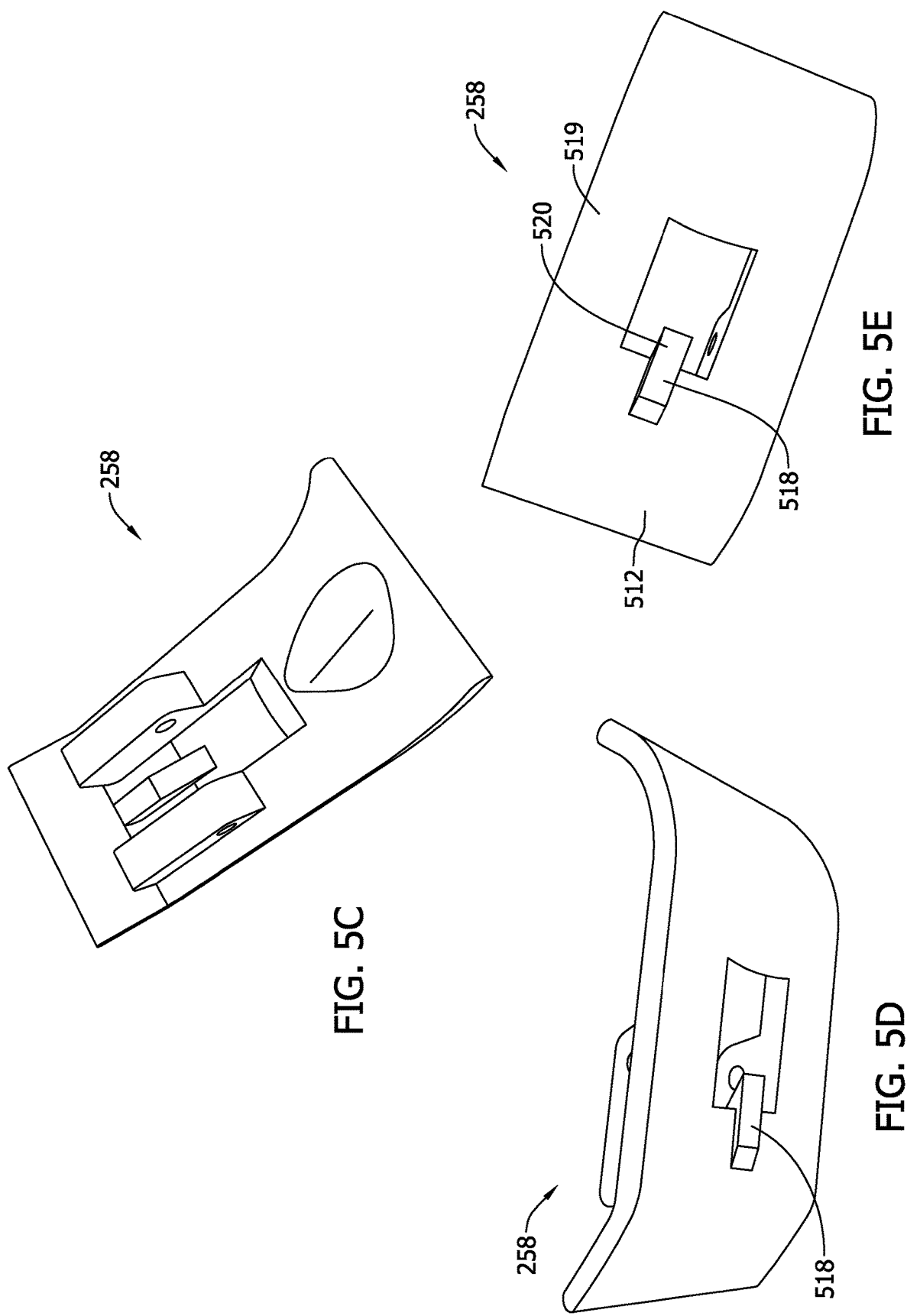

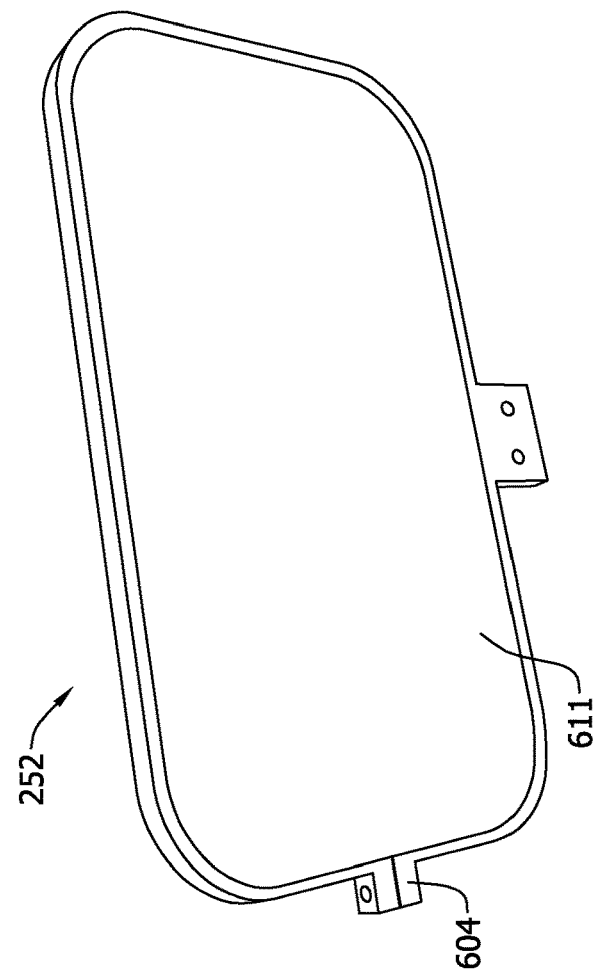
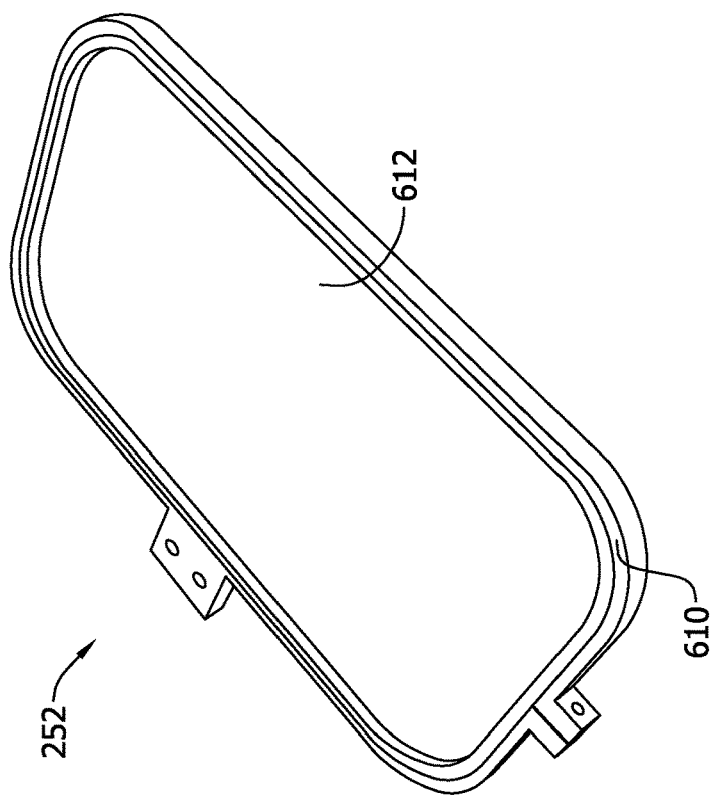
FIG. 6B
FIG. 6A 252-t

SYSTEMS, ASSEMBLIES, AND METHODS OF FABRICATION OF LIQUID METAL RADIO-FREQUENCY COIL ASSEMBLIES OF A MAGNETIC RESONANCE SYSTEM

BACKGROUND

The field of the disclosure relates generally to a magnetic resonance (MR) system, and more particularly, to radio frequency (RF) coil assemblies for an MR system.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

In MRI, an RF coil assembly is used to detect MR signals emitted from a subject and thus is a key component of an MR system. Known systems, assemblies, and methods of fabrication of RF coil assemblies are disadvantaged in some aspects and improvements are desired.

BRIEF DESCRIPTION

In one aspect, a method of fabricating a liquid metal radio-frequency (RF) coil assembly of a magnetic resonance (MR) system using a sewing machine is provided. The method includes providing a sewing accessory assembly, the sewing accessory assembly including a substrate holder and a presser foot. The method also includes attaching the presser foot with a sewing machine, positioning the substrate holder containing a first substrate underneath a needle arm of the sewing machine, and carving a pattern of grooves on a surface of the first substrate using the presser foot by operating the sewing machine. The method further includes forming RF coil loops by depositing liquid metal in the grooves and applying a second substrate over the RF coil loops.

In another aspect, a method of fabricating a liquid metal RF coil assembly of an MR system using a sewing machine is provided. The method includes providing a sewing accessory assembly, the sewing accessory assembly including a substrate holder. The substrate holder includes an inner hoop, an outer loop, and one or more coil loop supports configured to be coupled with the inner hoop and be positioned within the inner hoop. The method also includes coupling an RF coil loop filled with liquid metal on one of the one or more coil loop supports, and assembling a stretchable substrate with the substrate holder by securing the stretchable substrate between the inner hoop and the outer hoop. The method further includes coupling the assembled substrate holder with a sewing machine, and assembling a liquid metal RF coil assembly by sewing stitches to attach the RF coil loop with the stretchable substrate.

In one more aspect, a sewing accessory assembly of a sewing machine for fabricating an RF coil assembly of an MR system is provided. The sewing accessory assembly includes a presser foot. The presser foot includes a foot body including a top surface and a bottom surface opposite the top surface. The presser foot also includes a wedge positioned on the bottom surface and extending away from the foot body. The sewing accessory assembly also includes a substrate holder configured to be coupled with an embroidery hoop coupler of a sewing machine.

BRIEF DESCRIPTION OF DRAWINGS

Non-limiting and non-exhaustive embodiments are described with reference to the following figures, wherein like reference numerals refer to like parts throughout the various drawings unless otherwise specified.

FIG. 5A is a perspective view of an example presser foot of the sewing accessory assembly shown in FIG. 2B.

FIG. 5B is a side perspective view of the presser foot shown in FIG. 5A without depicting a pin.

FIG. 5C is a top perspective view of the presser foot shown in FIG. 5B.

FIG. 5D is a bottom perspective view of the presser foot shown in FIG. 5B.

FIG. 5E is a bottom view of the presser foot shown in FIG. 5B.

FIG. 6A is top perspective view of an example substrate holder of the sewing accessory assembly shown in FIG. 2B.

FIG. 6B is a bottom perspective view of the substrate holder shown in FIG. 6A.

DETAILED DESCRIPTION

Figure 1:
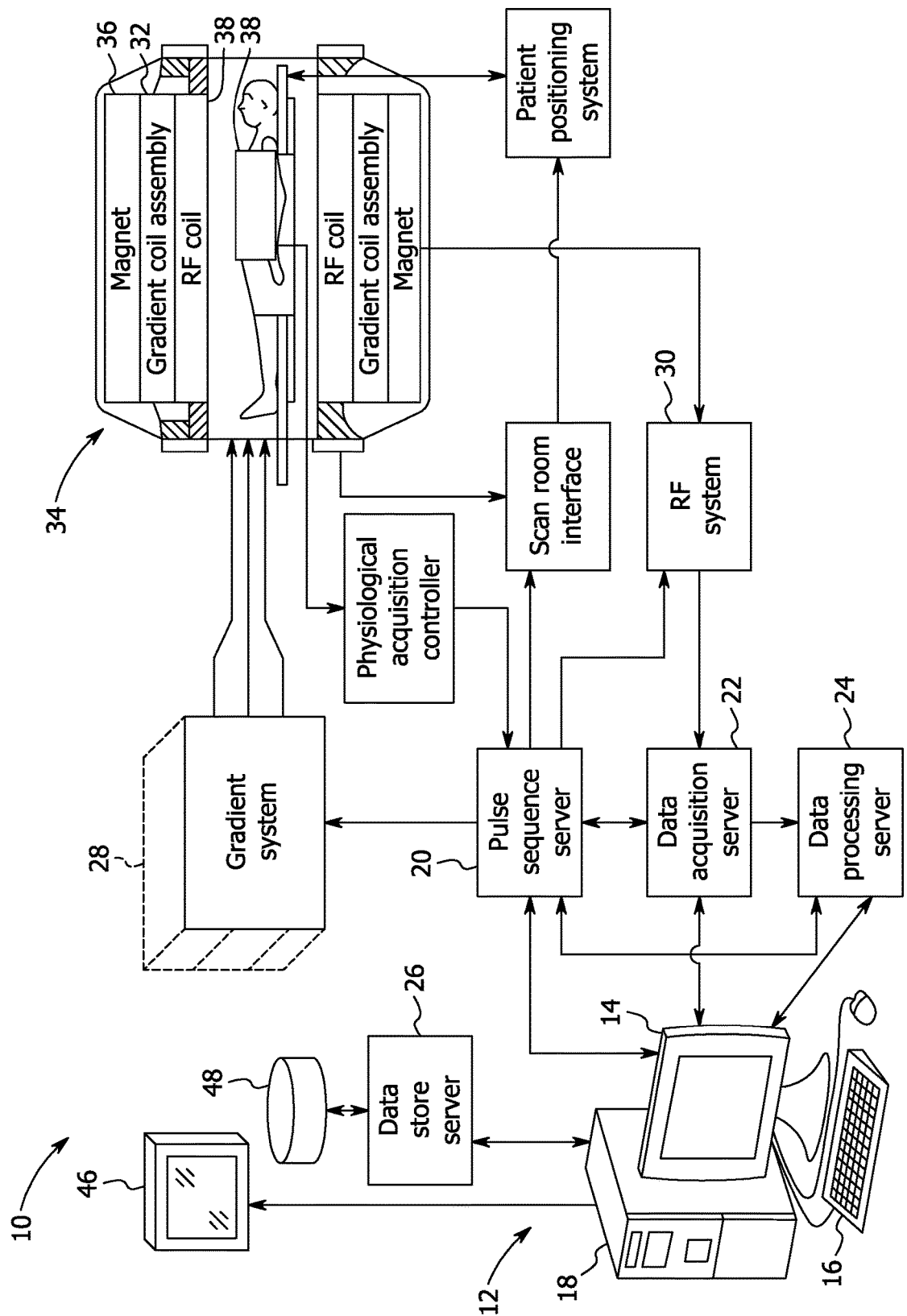
FIG. 1 is a block diagram of a magnetic resonance (MR) system.

The disclosure includes systems, assemblies, and methods of fabrication of liquid metal radio frequency (RF) coil assemblies for use in magnetic resonance (MR) systems for scanning a subject. As used herein, a subject is a human, an animal, a phantom, or any object scanned by a medical imaging system. MR imaging is described as an example only. The assemblies, systems, and methods described herein may be used for MR spectroscopy. MR systems are described as examples only. The systems, assemblies, and methods described herein may be used for medical imaging systems other than MR systems, such as positron emission tomography (PET)-MR systems. Liquid metal RF coil assemblies may also be used in transducers of MR guided focused ultrasound surgery (MRgfUS) systems. Liquid metal conductive leads may also be used in electroencephalography (EEG). Method aspects of assembling and using the RF coil assemblies will be in part apparent and in part explicitly discussed in the following description.

Coil loops of liquid metal RF coil assemblies are fabricated with liquid metal, instead of metal strips or metal wires. Liquid metal may be eutectic gallium indium. Liquid metal RF coil loops are stretchable by enclosing liquid metal in stretchable substrate, such as polymer, that exhibits viscoelasticity. Being stretchable is when the dimensions of the coil loop may be changed by applying force in one or more directions. Stretchable RF coils are advantageous in conforming with anatomy of the subject, thereby providing increased signal to noise ratio (SNR). Stretchable RF coils also provide increased subject comfort.

Fabricating liquid metal RF coils using known methods is tedious and time consuming. Known fabrication methods are largely manual, which are prone to errors and relatively slow, and therefore unsatisfactory for large-scale industry production. Using a mold is not practical because molds need to be created for each design of the coil. In a known method of screen printing, the major drawback of screen printing is that the fabricated RF coil assembly is not stretchable, because the liquid metal needs to be adhered to the substrate for screen printing to work. When the RF coil is being stretched, the liquid metal tends to crack, rendering the RF coil dysfunctional. Further, the equipment of screen printing is bulky and the process of screen printing is inflexible. Screens have to be made before the fabrication processes. Multiple coils need multiple screens. The emulsion on the screen may degrade over time. Multiple screens may be made for one design. To change the design of the RF coil, new screens need to be made. In one more known method, where tubes are filled with liquid metal and placed in casing formed by textiles, the RF coil does not stretch together with the textile to conform with the anatomy because the casing only provides a space for the RF coil but does not attach the RF coil with the textiles.

The methods and assemblies described herein overcome the above described problems in known methods. The methods and assemblies described herein include accessory assemblies to enable fabrication of liquid metal RF coil assemblies using a sewing machine. As used herein, a sewing machine is a machine that drives a needle to produce stitches on a material, and may be a regular sewing machine, an embroidery machine, or a combination of both. The speed of fabrication is increased. For example, fabricating a coil loop may take a few minutes with the methods, systems, and assemblies described herein, as compared to hours in known methods. Fabricating liquid metal RF coil assemblies using a sewing machine as described herein is advantageous than other known methods in providing liquid metal RF coil assemblies with increased quality, where the sewing machine has more precise and finer control of the movement, the pattern, and/or attachment of the stretchable material with the coil loop, during the fabrication process than a human or in other methods. The systems, assemblies, and methods described herein enable industry-scale fabrication of RF coil assemblies with reduced time and increased quality. Besides automizing the fabrication, the systems, assemblies, and methods are advantageous in providing customized fabrication of liquid metal RF coil assemblies. The designs of the RF coil loops may be input into the sewing machine. To customize the design, only design files needs to be modified, which reduces costs and labor associated with molds or screens in known methods.

In MR imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MR image, a magnetic field (referred to as an excitation field B1), which is in the x-y plane and near the Larmor frequency, is generated by an RF coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses ($G_x$, $G_y$, and $G_z$) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

FIG. 1 illustrates a schematic diagram of an example MR system 10. In the example embodiment, MR system 10 includes a workstation 12 having a display 14 and a keyboard 16. Workstation 12 includes a processor 18, such as a commercially available programmable machine running a commercially available operating system. Workstation 12 provides an operator interface that allows scan prescriptions to be entered into MR system 10. Workstation 12 is coupled to a pulse sequence server 20, a data acquisition server 22, a data processing server 24, and a data store server 26. Workstation 12 and each server 20, 22, 24, and 26 communicate with each other.

In the example embodiment, pulse sequence server 20 responds to instructions downloaded from workstation 12 to operate a gradient system 28 and an RF system 30. The instructions are used to produce gradient and RF waveforms in MR pulse sequences. An RF coil assembly 38 and a gradient RF coil assembly 32 are used to perform the prescribed MR pulse sequence. RF coil assembly 38 may be a whole body RF coil. RF coil assembly 38 may also be a local RF coil assembly 38 that may be placed in proximity to the anatomy to be imaged, or a coil array that includes a plurality of coils.

In the example embodiment, gradient waveforms used to perform the prescribed scan are produced and applied to gradient system 28, which excites gradient coils in gradient RF coil assembly 32 to produce the magnetic field gradients $G_x$, $G_y$, and $G_z$ used for position-encoding MR signals. Gradient RF coil assembly 32 forms part of a magnet assembly 34 that also includes a polarizing magnet 36 and RF coil assembly 38.

In the example embodiment, RF system 30 includes an RF transmitter for producing RF pulses used in MR pulse sequences. The RF transmitter is responsive to the scan prescription and direction from pulse sequence server 20 to produce RF pulses of a desired frequency, phase, and pulse amplitude waveform. The generated RF pulses may be applied to RF coil assembly 38 by RF system 30. Responsive MR signals detected by RF coil assembly 38 are received by RF system 30, amplified, demodulated, filtered, and digitized under direction of commands produced by pulse sequence server 20. RF coil assembly 38 is described as a transmit and receive coil such that RF coil assembly 38 transmits RF pulses and detects MR signals. In one embodiment, MR system 10 may include a transmit RF coil that transmits RF pulses and a separate receive coil that detects MR signals. A transmission channel of RF system 30 may be connected to an RF transmit coil and a receiver channel may be connected to a separate RF receive coil. Often, the transmission channel is connected to the whole body RF coil assembly 38 and each receiver section is connected to a separate local RF coil.

In the example embodiment, RF system 30 also includes one or more RF receiver channels. Each RF receiver channel includes an RF amplifier that amplifies the MR signal received by RF coil assembly 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M = \sqrt{I^2 + Q^2}; \quad (1)$$

and the phase of the received MR signal may also be determined as in Eq. (2) below:

$$\varphi = \tan^{-1}\left(\frac{Q}{I}\right). \quad (2)$$

In the example embodiment, the digitized MR signal samples produced by RF system 30 are received by data acquisition server 22. Data acquisition server 22 may operate in response to instructions downloaded from workstation 12 to receive real-time MR data and provide buffer storage such that no data is lost by data overrun. In some scans, data acquisition server 22 does little more than pass the acquired MR data to data processing server 24. In scans that need information derived from acquired MR data to control further performance of the scan, however, data acquisition server 22 is programmed to produce the needed information and convey it to pulse sequence server 20. For example, during prescans, MR data is acquired and used to calibrate the pulse sequence performed by pulse sequence server 20. Also, navigator signals may be acquired during a scan and used to adjust the operating parameters of RF system 30 or gradient system 28, or to control the view order in which k-space is sampled.

In the example embodiment, data processing server 24 receives MR data from data acquisition server 22 and processes it in accordance with instructions downloaded from workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the example embodiment, images reconstructed by data processing server 24 are conveyed back to, and stored at, workstation 12. In some embodiments, real-time images are stored in a database memory cache (not shown in FIG. 1), from which they may be output to operator display 14 or a display 46 that is located near magnet assembly 34 for use by attending physicians. Batch mode images or selected real time images may be stored in a host database on disc storage 48 or on a cloud. When such images have been reconstructed and transferred to storage, data processing server 24 notifies data store server 26. Workstation 12 may be used by an operator to archive the images, produce films, or send the images via a network to other facilities.

During a scan, interfacing cables may be used to transmit signals between RF coil assembly 38 and other aspects of MR system 10 (e.g., RF system 30, data acquisition server 22, and pulse sequence server 20), for example to control the RF coils and/or to receive signals from the RF coils. As described above, the RF coil assembly 38 may be a transmit coil that transmits RF excitation signals, or a receive coil that receives the MR signals emitted by the subject. In an example, the transmit and receive coils are a single mechanical and electrical structure or array of structures, with transmit/receive mode switchable by auxiliary circuitry. In other examples, a transmit coil and a receive coil may be independent structures that are physically coupled to each other via the RF system 30. For enhanced image quality, however, a receive coil is desirable to be mechanically and electrically isolated from the transmit coil. In such cases, the receive coil in the receive mode is electromagnetically coupled to and resonant with an RF "echo" that is stimulated by the transmit coil. On the other hand, during a transmit mode, the receive coil is electromagnetically decoupled from and therefore not resonant with the transmit coil, during transmission of the RF signal. Such decoupling averts a potential problem of noise produced within the auxiliary circuitry when the receive coil couples to the full power of the RF signal.

A traditional receive coil for MR includes several conductive intervals joined between themselves by capacitors. By adjusting the capacitors' values, the impedance of the RF coil may be brought to its minimal value, usually characterized by a low resistance. At a resonant frequency, stored magnetic and electric energy alternate periodically. Each conductive interval, due to its length and width, possesses a certain self-capacitance, where electric energy is periodically stored as static electricity. The distribution of this electricity takes place over the entire conductive interval length in the order of 5-15 cm, causing similar range electric dipole field. In proximity of a large dielectric load, self-capacitance of the intervals change, resulting in detuning of the coil. In case of a lossy dielectric, dipole electric field causes Joule dissipation characterized by an increased overall resistance observed by the coil.

Traditional RF coils may include acid etched copper traces or loops on printed circuit boards (PCBs) with lumped electronic components (e.g., capacitors, inductors, baluns, and resisters), matching circuitry, decoupling circuitry, and pre-amplifiers. Such a configuration is typically bulky, heavy, and rigid, and requires relatively strict placement of the coils relative to each other in an array to prevent coupling interactions among coil elements that may degrade image quality. As such, traditional RF coils and RF coil arrays lack flexibility and therefore may not conform to subject anatomy, degrading imaging quality and subject comfort.

Figure 2A:
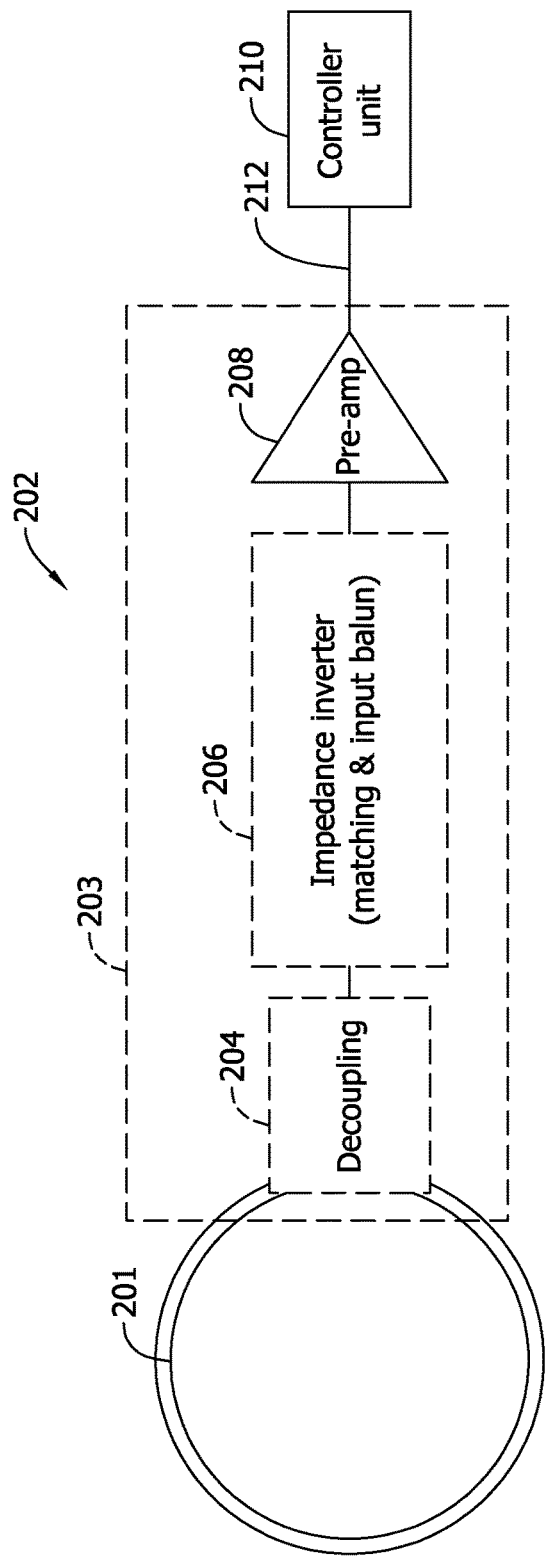
FIG. 2A is a block diagram of an example radio-frequency (RF) coil assembly.

FIG. 2A is a block diagram of an example RF coil 202. In the example embodiment, RF coil 202 includes coil loop 201 coupled to a controller unit 210 via a coupling electronics portion 203 and a coil-interfacing cable 212. Coil loop 201 is formed by liquid metal (see FIGS. 3A and 3B described later). The length and the design of coil loop 201 is varied to achieve a select distributed capacitance (DCAP), and accordingly, a select resonance frequency. DCAP, as used herein, represents a capacitance exhibited between conductors that grows evenly and uniformly along the length of the conductors and is void of discrete or lumped capacitive components and discrete or lumped inductive components. In one example, the RF coil may be a surface receive coil, which may be single- or multi-channeled. RF coil 202 may operate at one or more frequencies in MR system 10. Coil-interfacing cable 212 may be a coil-interfacing cable extending between coupling electronics portions 203 or between an RF coil assembly and other components of MR system 10 such as RF system 30.

In the example embodiment, coupling electronics portion 203 may be coupled to coil loop 201 of RF coil 202. Coupling electronics portion 203 may include a decoupling circuit 204, impedance inverter circuit 206, and a pre-amplifier 208. Decoupling circuit 204 may effectively decouple the RF coil during a transmit operation. Typically, RF coil 202 in the receive mode may be positioned adjacent a body of a subject being imaged by MR system 10 in order to receive echoes of the RF signal transmitted during the transmit mode. If RF coil 202 is not used for transmission, RF coil 202 is decoupled from the RF transmit coil such as the RF body coil when the RF transmit coil is transmitting the RF signal. The decoupling of the receive coil from the transmit coil may be achieved using resonance circuits and PIN diodes, microelectromechanical systems (MEMS) switches, or another type of switching circuitry. The switching circuitry may activate detuning circuits operatively connected to RF coil 202.

In the example embodiment, the impedance inverter circuit 206 may form an impedance matching network between RF coil 202 and pre-amplifier 208. Impedance inverter circuit 206 is configured to transform a coil impedance of RF coil 202 into an optimal source of impedance for pre-amplifier 208. The impedance inverter circuit 206 may include an impedance matching network and an input balun. Pre-amplifier 208 receives MR signals from corresponding RF coil 202 and amplifies the received MR signals. In one example, the pre-amplifier may have a low input impedance that is configured to accommodate a relatively high blocking or source impedance. Coupling electronics portion 203 may be packaged in a small PCB with a surface area of approximately 2 cm$^2$ or smaller. The PCB may be protected with a conformal coating or an encapsulating resin.

Coil-interfacing cable 212 may be used to transmit signals between the RF coils and other components of MR system 10. The coil interfacing cables may be disposed within the bore or imaging space of MR system 10. In MR systems, coil-interfacing cables 212 may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents.

Figure 2B:
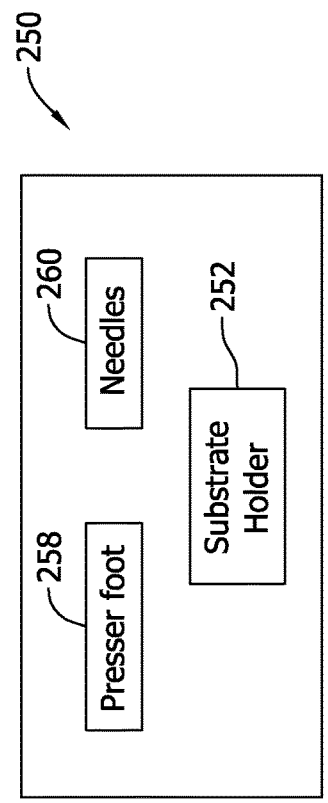
FIG. 2B is an example sewing accessory assembly for fabricating a liquid metal RF coil assembly.
Figure 2C:
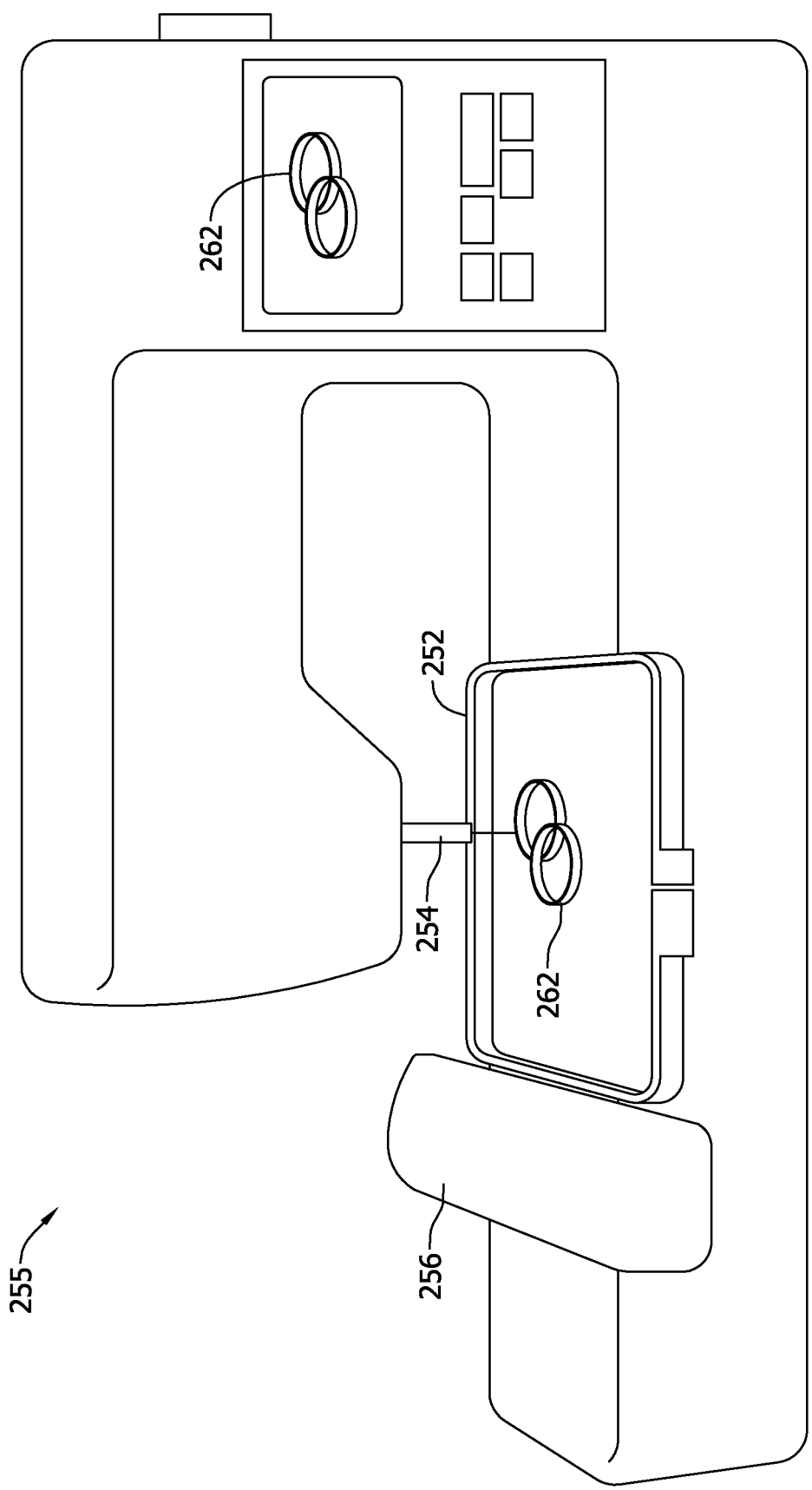
FIG. 2C shows a sewing machine.

FIG. 2B is a schematic diagram of an example sewing accessory assembly 250. FIG. 2C shows a sewing machine. In the example embodiment, sewing accessory assembly 250 includes a substrate holder 252 configured to be used on a sewing machine 255. Substrate holder 252 is configured to couple with an embroidery hoop coupler 256 (FIG. 2C) of sewing machine 255. Sewing accessory assembly 250 may further include a presser foot 258. Sewing accessory assembly 250 may also include needles 260. Individual components and subparts of individual components may be fabricated with additive manufacturing.

Figure 3B:
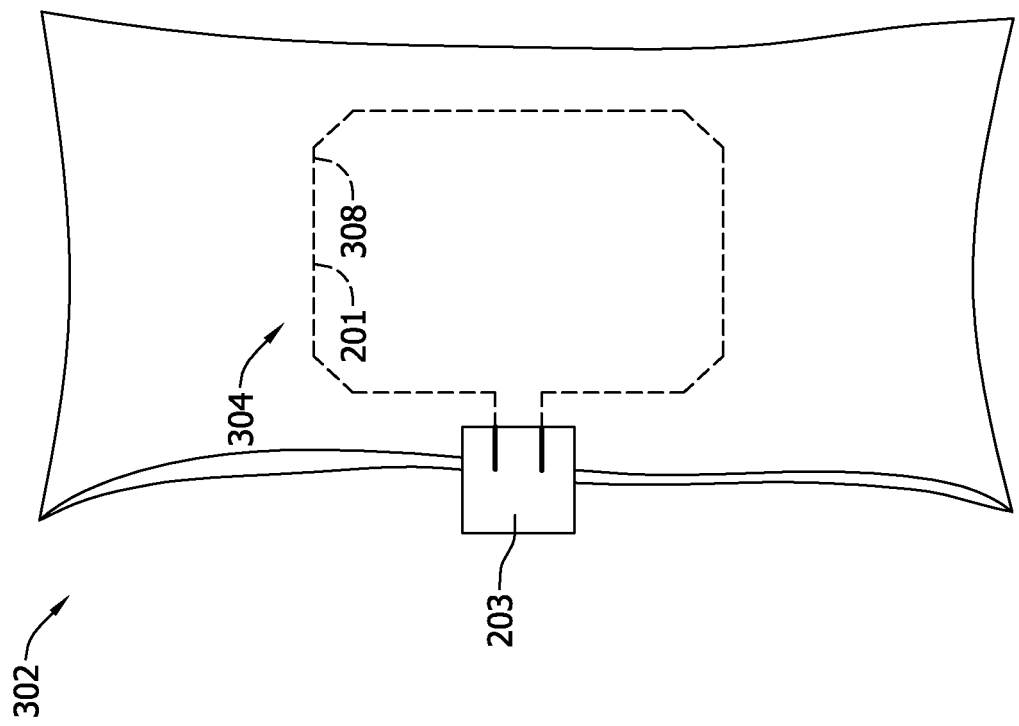
FIG. 3B illustrates the liquid metal RF coil assembly shown in FIG. 3A when being stretched.
Figure 3A:
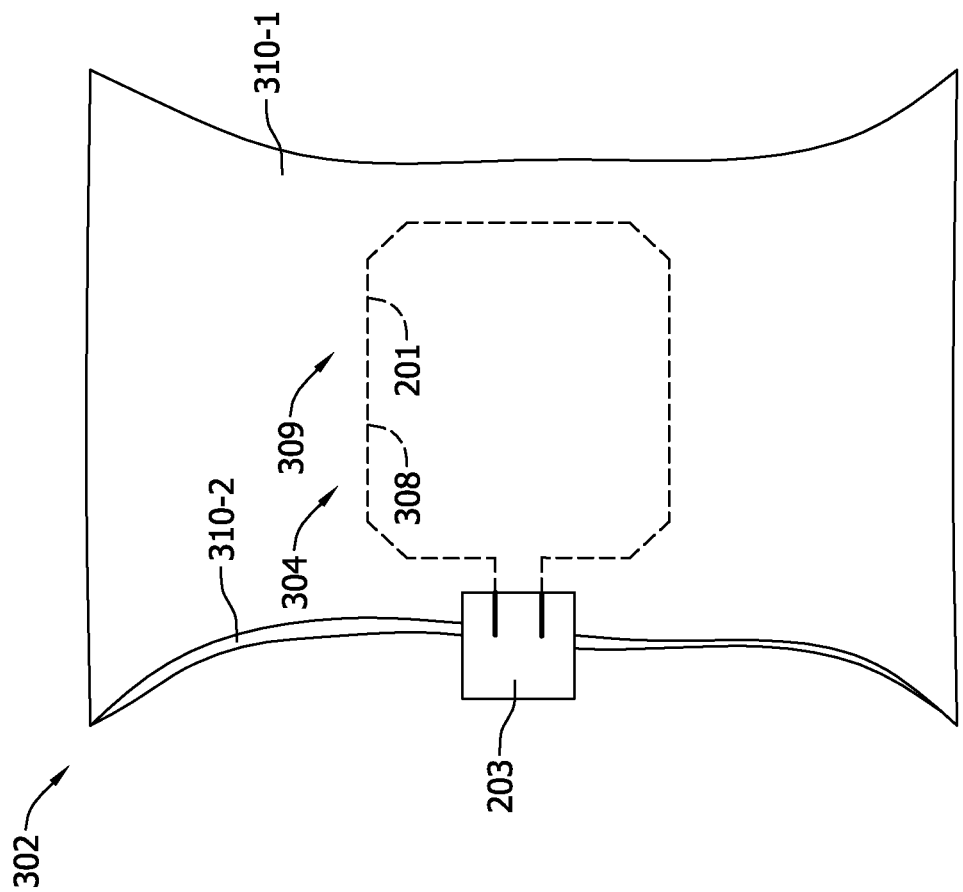
FIG. 3A shows an example liquid metal RF coil assembly.

FIGS. 3A and 3B show an example RF coil assembly 302. In the example embodiment, RF coil assembly 302 includes RF coil 304. RF coil 304 includes coil loop 201 and coupling electronics portion 203. Coil loop 201 is formed by liquid metal 308. RF coil assembly 302 further includes a first substrate 310-1 and a second substrate 310-2. First substrate 310 and second substrate 310 may be fabricated with the same material or different material. First substrate 310 and second substrate 310 are stretchable in multiple directions. Example material of substrate 310 may be polymer. Liquid metal 308 is sandwiched between first substrate 310 and second substrate 310. Because coil loop 201 is formed by liquid metal 308, coil loop 201 is stretchable. FIG. 3A shows RF coil assembly 302 without force being applied. FIG. 3B shows dimensions of coil loop 201 are changed when coil loop 201 is stretched, where the dimension in one direction is increased while the dimension in the other dimension is decreased.

Figure 4:
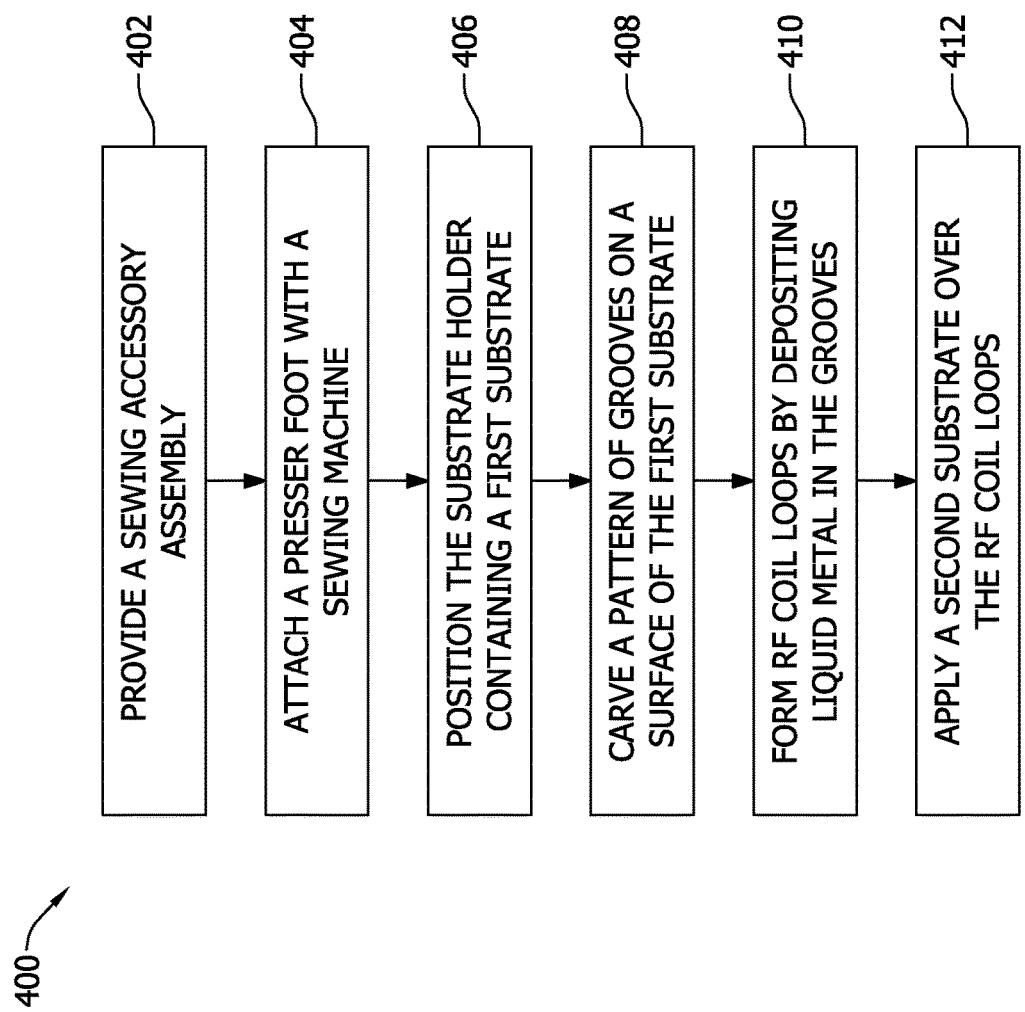
FIG. 4 is a flow chart of an example method of fabricating a liquid metal RF coil assembly.

FIG. 4 is a flow chart of an example method 400 of fabricating liquid metal RF coil assembly. In the example embodiment, method 400 includes providing 402 a sewing accessory assembly. Sewing accessory assembly 250 may include a presser foot 258. Sewing accessory assembly 250 may further include one or more needles 260. Sewing accessory assembly 250 may also include a substrate holder 252. The elements in sewing accessory assembly 250 are configured to be coupled with a sewing machine such that at least part of the RF coil assembly is fabricated with a sewing machine.

FIGS. 5A-5E show example presser foot 258. FIG. 5A is a perspective view of presser foot 258. FIGS. 5B-5E show various views of presser foot 258 without depicting a pin 502. FIG. 5B is a side perspective view. FIG. 5C is top perspective views. FIG. 5D is a bottom perspective view. FIG. 5E is a bottom view.

In the example embodiment, presser foot 258 includes a foot body 504 and pin 502. Pin 502 is configured to be coupled or attached with a presser holder (not shown) of a sewing machine such that presser foot 258 is attached to the presser foot holder when presser foot 258 is used during sewing. Foot body 504 includes pin apertures 508 (FIG. 5B) sized to receive ends of pin 502 therein.

In the example embodiment, foot body 504 includes a top surface 510 and a bottom surface 512. Bottom surface 512 is generally smooth. Foot body 504 also includes a front end 514 and a back end 516. Foot body 504 curves upwards at front end 514. Foot body 504 further includes a wedge 518 extending from bottom surface 512 and away from foot body 504. Wedge 518 may have a curved end such that a curved groove is carved in first substrate 310. For example, wedge 518 may be curved toward a side 519 of foot body 504 such that an end 520 of wedge 518 points toward side 519. When presser foot 258 is placed on a generally flat surface such as substrate holder 252 (see FIG. 2C), without wedge 518, presser foot 258 would glide along the surface like a typical presser foot of a sewing machine. With wedge 518, wedge 518 will contact substrate holder 252 before bottom surface 512, thereby scratching substrate holder 252 and carving out grooves 309 (FIG. 3A) during sewing.

Figure 6C:
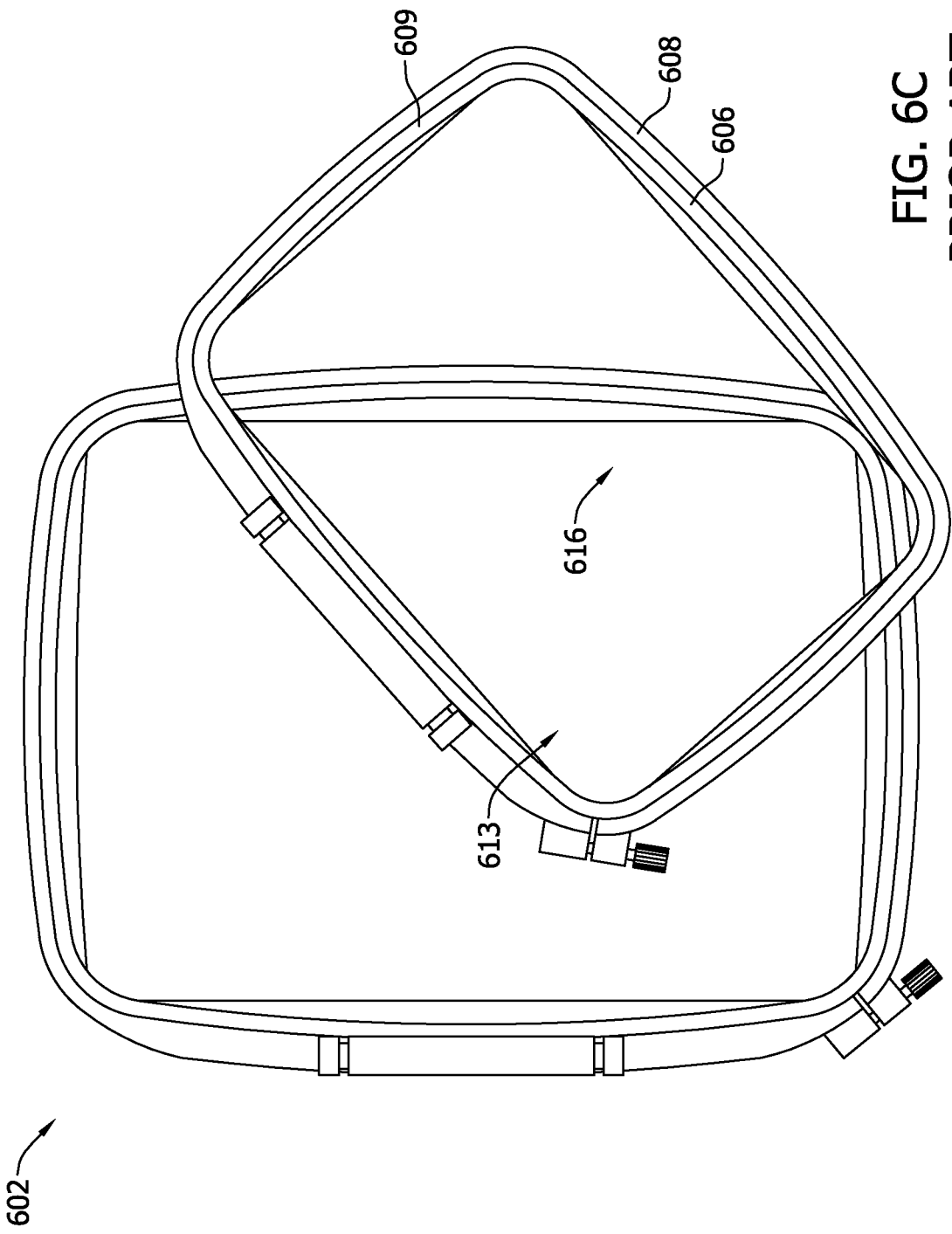
FIG. 6C shows known embroidery hoops.

FIGS. 6A and 6B show example substrate holder 252. FIG. 6A is a top perspective view of substrate holder 252. FIG. 6B is a bottom perspective view of substrate holder 252. FIG. 6C shows a typical known embroidery hoop 602. In the example embodiment, substrate holder 252 is configured to fit with a sewing machine like typical embroidery hoop 602. Substrate holder 252 includes brackets 604 configured to be coupled with a hoop coupler 256 of sewing machine 255. Substrate holder 252 has a dimension that is suitable to be used with a sewing machine. For example, substrate holder 252 may have a dimension of 28 inches (in.) (71 cm) by 15 in. (38 cm).

In a typical embroidery hoop 602, embroidery hoop 602 includes an inner hoop 606 and an outer hoop 608. Embroidery hoop 602 forms a loop 609 and defines an aperture 613 such that a fabric is held by embroidery hoop 602 and stretched over aperture 613. Stitches are formed on the fabric within hoop 602.

In the example embodiment, unlike embroidery hoop 602, substrate holder 252 does not have an aperture. Instead, substrate holder 252 includes edges 610 and a bottom 611 extending between edges 610. Bottom 611 and edge 610 define a receptacle 612 sized to receive substrate 310 (FIG. 3A) therein. Bottom 611 is concave away from edges 610 such that substrate holder 252 defines receptacle 612. Receptacle 612 does not include apertures such that liquid is contained therein. A substrate 310 may be polymer. Polymer may be liquid and be poured into receptacle 612 of substrate holder 252. Polymer may be hardened by a curing process.

Figure 7C:
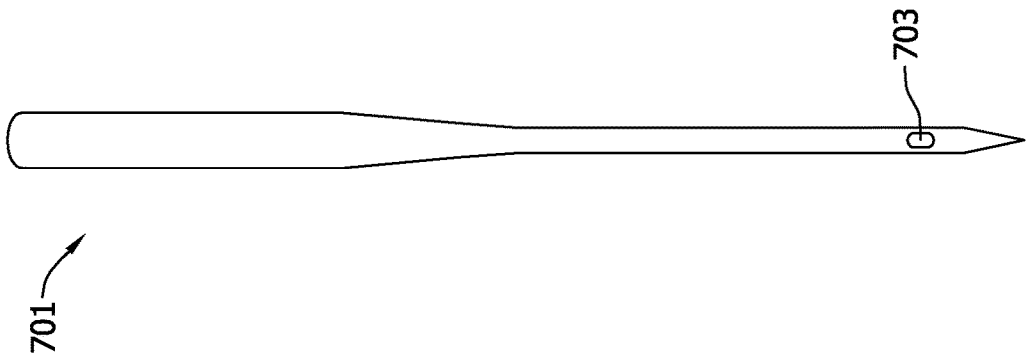
FIG. 7C shows known sewing needles for use in a sewing machine.
Figure 7B:
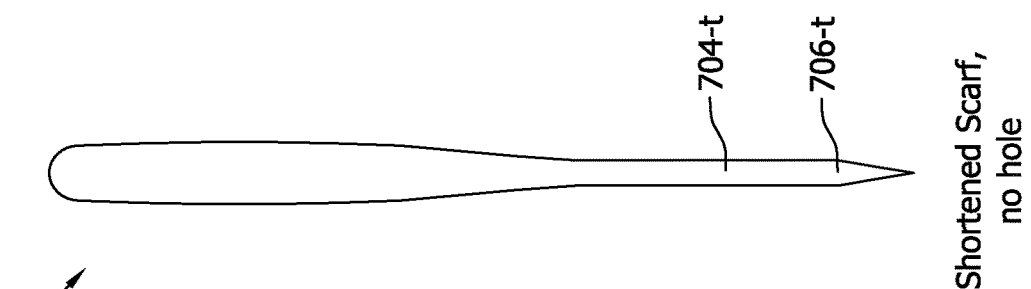
FIG. 7B shows another example needle of the sewing accessory assembly shown in FIG. 2B.
Figure 7A:
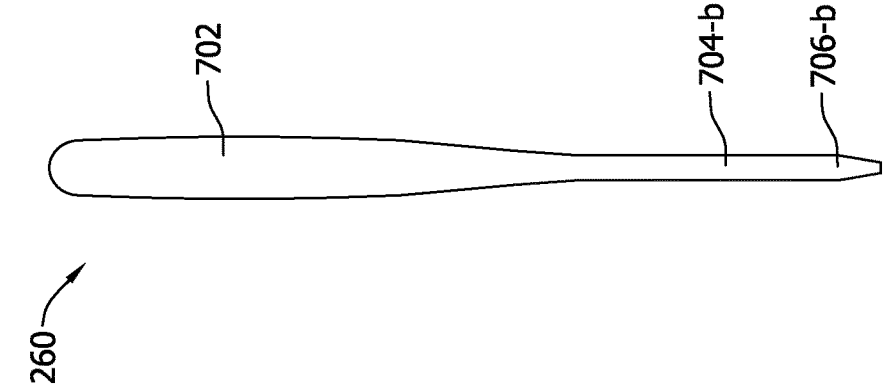
FIG. 7A shows an example needle of the sewing accessory assembly shown in FIG. 2B.

FIGS. 7A and 7B shows example needles 260 of sewing accessory assembly 250. FIG. 7C shows a typical known sewing needle 701. In the example embodiment, needle 260 does not include an eye 703, unlike known needle 701. Needle 260 may be shorter than known sewing needles 701 to accommodate the thickness of first substrate 310. Needle 260 includes a needle body 702 and needle tip 704. Needle tip 704 extends from needle body 702. Needle tip 704 may have a blunt end 706-$b$. Needle tip 704 may have a tapered end 706-$t$ such that the needle tip 704 with a tapered end 706-$t$ produces apertures having a size smaller than apertures produced by blunt end 706-$b$.

Referring back to FIG. 4, in the example embodiment, method 400 of fabricating a liquid metal RF coil assembly further includes attaching 404 a presser foot with a sewing machine. Presser foot 258 may be attached to a presser foot holder by pin 502 of presser foot 258 being snapped and received into a shank of the presser foot holder. A first substrate 310 may be placed into substrate holder 252. First substrate 310 may be in a liquid state. First substrate 310 may be cured to be hardened with mechanisms such as heat, radiation, or electron beams. After being cured, first substrate 310 may be in a gel-like state such that first substrate 310 remains stretchable while has a defined shape and be used to hold liquid metal therein.

In the example embodiment, method 400 further includes positioning 406 the substrate holder containing the first substrate. Substrate holder 252 may be placed underneath the presser foot 258. Alternatively, substrate holder 252 may be placed on a platform of the sewing machine that is underneath the needle arm 254 before presser foot 258 and/or the presser foot holder is attached to sewing machine 255. Substrate holder 252 may be coupled with embroidery hoop coupler 256 of sewing machine 255. When installed, bottom surface 512 of presser foot 258 and wedge 518 of presser foot 258 face substrate holder 252. The height of presser foot 258 may be adjusted based on the thickness of first substrate 310 and the desired groove depth in first substrate 310.

In the example embodiment, method 400 further includes carving 408 a pattern of grooves on a surface of the first substrate using the presser foot. An operator of the sewing machine may choose a pattern 262 (FIG. 2C) to be carved in first substrate 310. Alternatively, the operator may manually operate sewing machine 255 to carve out a pattern 262 directly onto first substrate 310. Because wedge 518 extends out of bottom surface 512, wedge 518 carves out grooves on first substrate 310. In some embodiment, needle 260 may be attached to needle arm 254. When sewing machine 255 is running, needle 260 produces apertures in first substrate 310 as needle 260 moves in and out of first substrate 310 during sewing. The produced apertures loosens first substrate 310, reducing the force needed to carver grooves by wedge 518. The sizes of apertures may be reduced by using needle 260 having tapered needle tip 704-$t$ in place of needle 260 having blunt needle tip 704-$b$.

In the example embodiment, method 400 further includes forming 410 RF coil loops by depositing liquid metal in the grooves. Method 400 further includes applying 412 a second substrate over the RF coil loops such that the liquid metal is sealed between the first substrate and the second substrate. Electronics and/or cables, such as coupling electronics portion 203 and/or coil-interfacing cable 212 may be electrically coupled with RF coil loop 201.

Figure 8C:
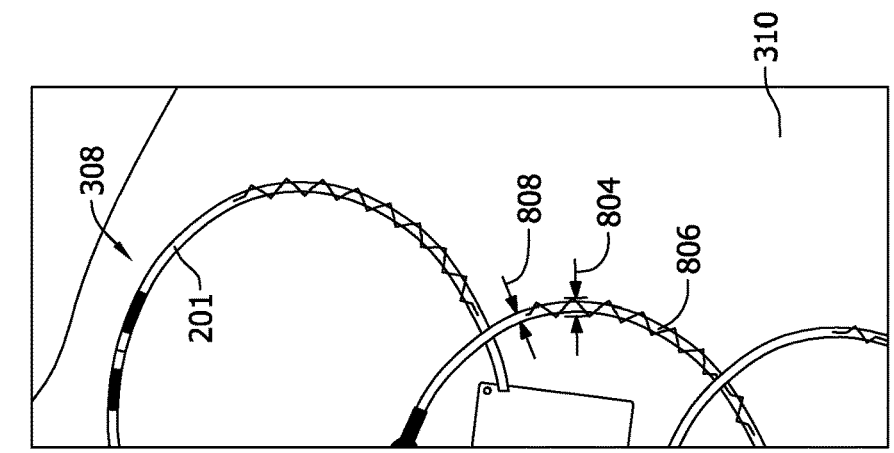
FIG. 8C shows the liquid metal RF coils assembled with a substrate using the methods described herein.
Figure 8B:
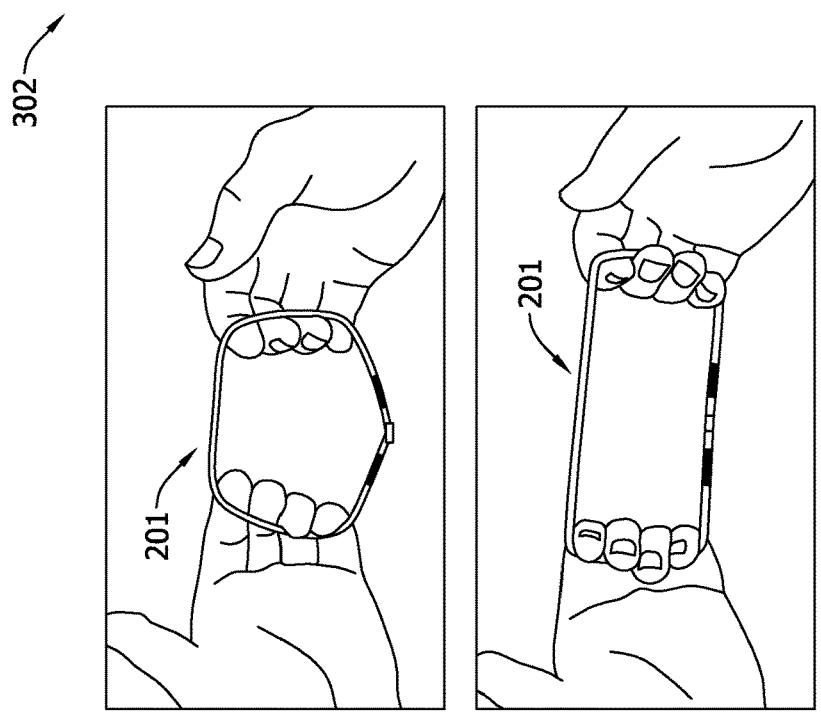
FIG. 8B shows RF coil loops of the liquid metal RF coil shown in FIG. 8A.
Figure 8A:
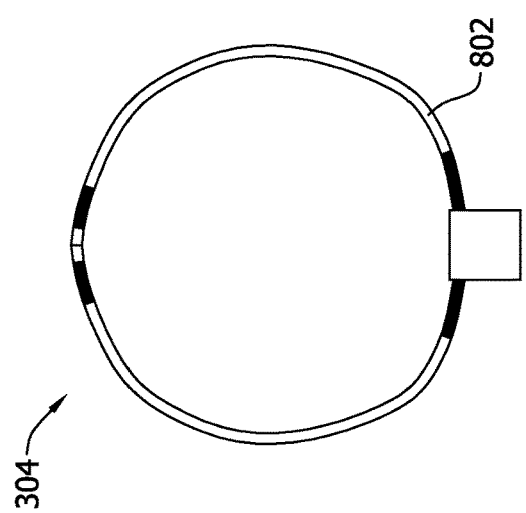
FIG. 8A shows another example liquid metal RF coil.

FIGS. 8A-8C shows another example liquid metal RF coil assembly 302. FIG. 8A shows RF coil 304. FIG. 8B shows coil loop 201. FIG. 8C shows coil loops 201 are assembled with a stretchable substrate 310. In the example embodiment, RF coil loops 201 are coupled with stretchable substrate 310 using stitches 806 being sewed on stretchable substrate 310 and around RF coil loops 201. RF coil loop 201 includes a tube 802 filled with liquid metal 308. RF coil loops 201 is stretchable. In fabricating liquid metal RF coil assemblies 302, stitches should not puncture tube 802, otherwise rendering RF coil loop 201 defective as liquid metal 308 leaks out of the punctures. Further, the spatial design and overlapping between RF coil loops need to be kept according to the design of the RF coil assemblies to provide optimized performance of RF coil assemblies in terms of signal to noise ratio (SNR) and decoupling between neighboring RF coil loops 201. Known fabrication methods do not meet these needs.

Figure 9:
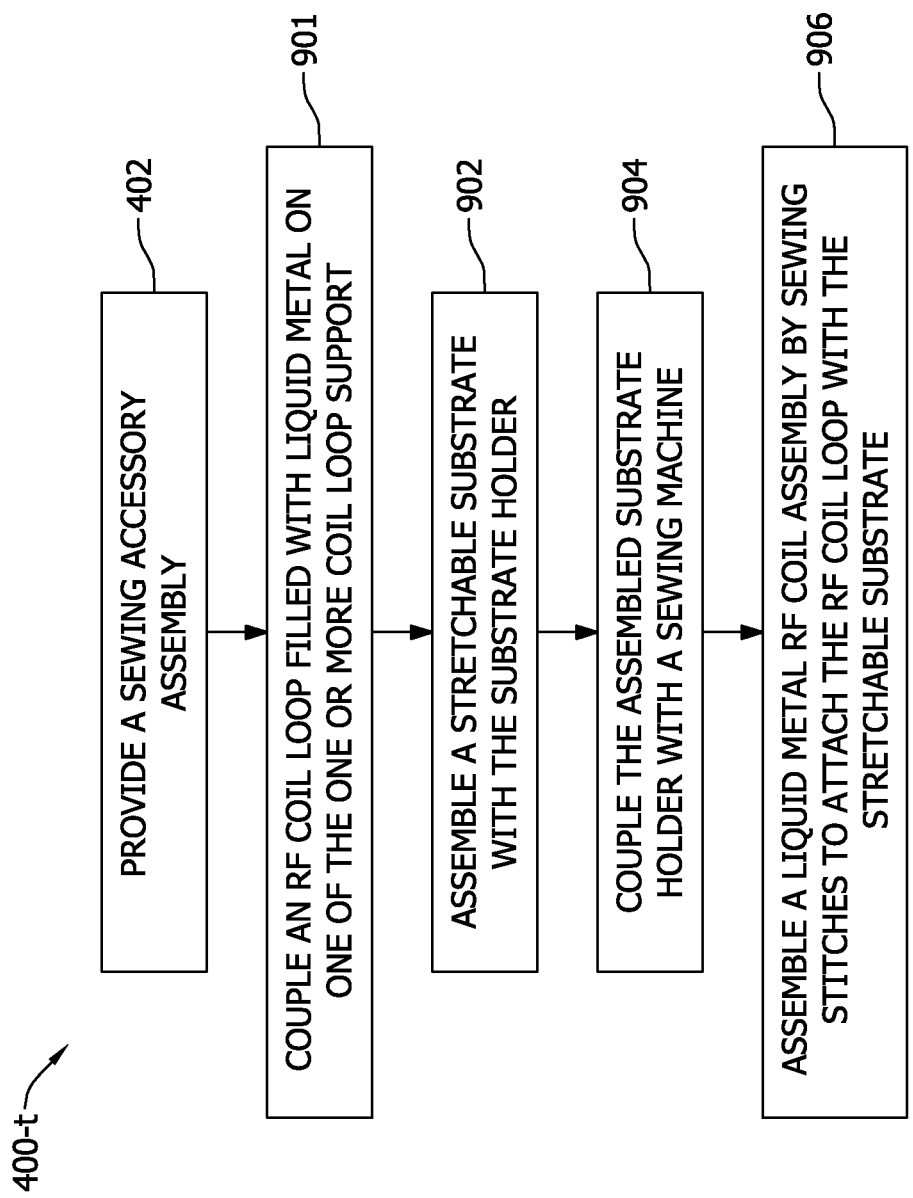
FIG. 9 is a flow chart of another example method of fabricating a liquid metal RF coil assembly.

FIG. 9 is a flow chart of another example method 400-$t$ of fabricating a liquid metal RF coil assembly. Method 400-$t$ includes providing 402 a sewing accessory assembly. Sewing accessory assembly 250 may include a presser foot 258-$c$ (see FIGS. 10A-10E described below).

Figure 10B:
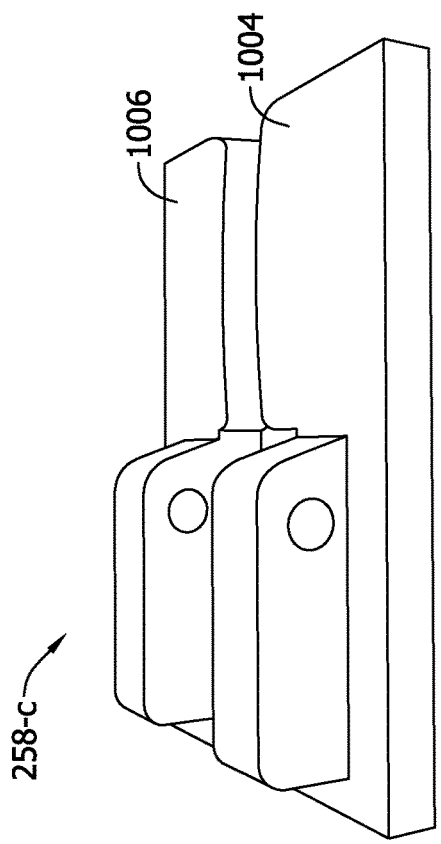
FIG. 10B is a side perspective view of the presser foot shown in FIG. 10A without depicting a pin.
Figure 10A:
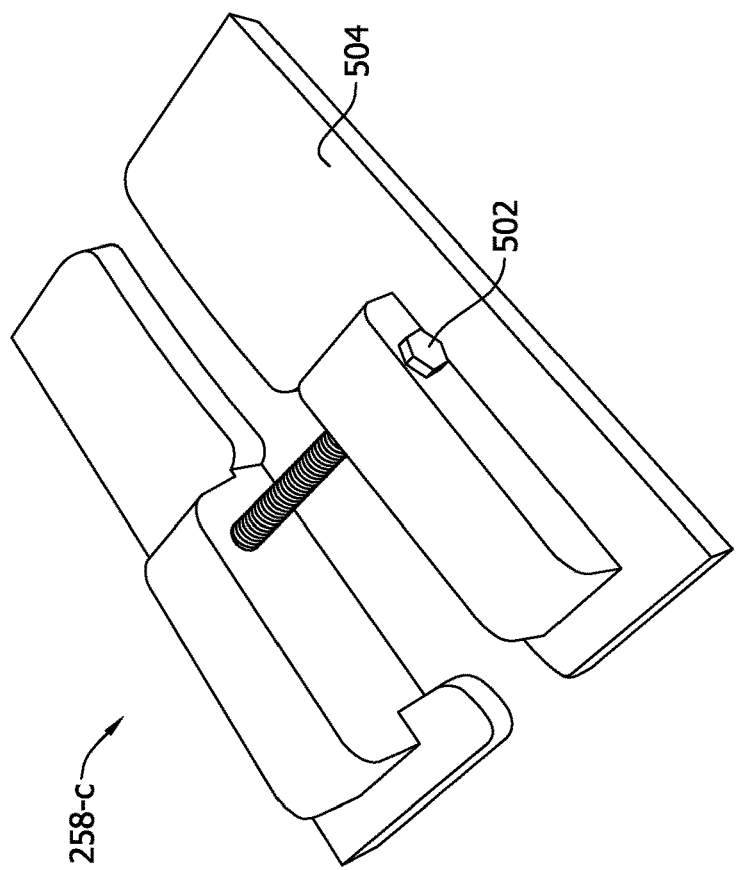
FIG. 10A is a top perspective view of another example presser foot of the sewing accessory assembly shown in FIG. 2B.
Figure 10C:
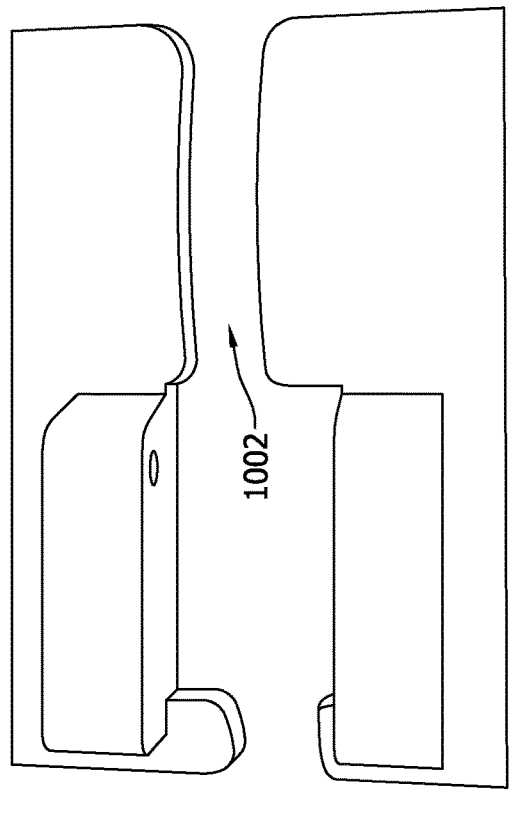
FIG. 10C is a top perspective view of the presser foot shown in FIG. 10B.
Figure 10D:
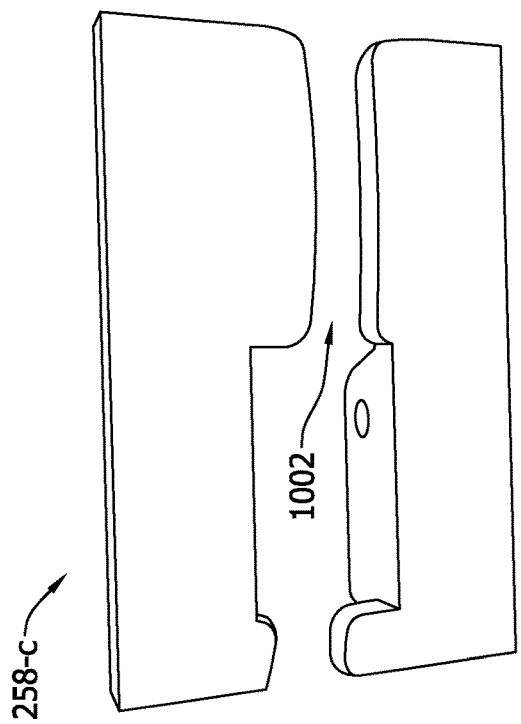
FIG. 10D is a bottom perspective view of the presser foot shown in FIG. 10B.
Figure 10E:
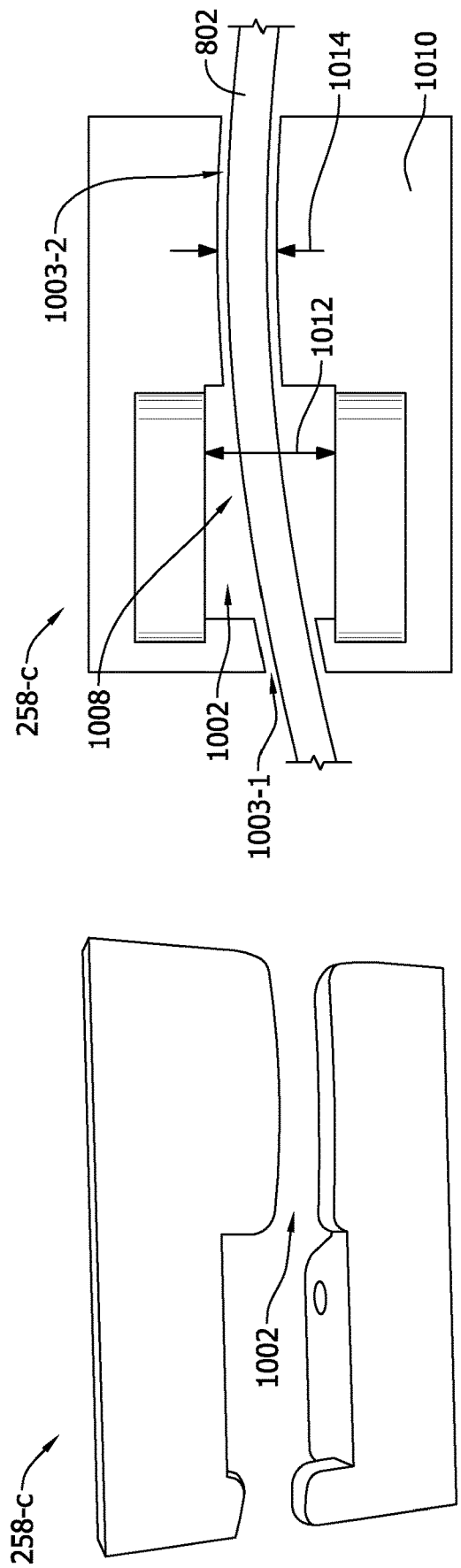
FIG. 10E is top view of the presser foot shown in FIG. 10B with a tube placed along a channel defined by the presser foot.

FIGS. 10A-10E show another example presser foot 258-$c$. FIG. 10A is a top perspective view of presser foot 258-$c$. FIGS. 10B-10E are various views of presser foot 258-$c$ without depicting pin 502. In the example embodiment, foot body 504 of presser foot 258 defines a channel 1002. Channel 1002 may be curved. In some embodiments, channel 1002 is straight. Foot body 504 includes a first portion 1004 and a second portion 1006 positioned separate from one another and define channel 1002. First portion 1004 and second portion 1006 may be discreet pieces. In some embodiments, first portion 1004 and second portion 1006 are connected via an intermediate portion (not shown) and channel 1002 is defined on the intermediate portion. Channel 1002 is sized to receive a section of a tube 802 therethrough. Channel 1002 includes a first end channel 1003-1 and a second end channel 1002-2 separated by needle aperture 1008. First end channel 1003-1 and second end channel 1003-2 are curved in the same direction. For example, when viewed from a side 1010 (FIG. 10E) presser foot 258, first end channel 1003-1 and second end channel 1003-2 are both concave. As a result, the section of coil loop 201 received in channel 1002 does not change between being concave and being convex. Channel 1002 further includes needle aperture 1008 having a first width 1012 greater than a second width 1014 of the rest of channel 1002. Needle aperture 1008 is positioned between first end channel 1003-1 and second end channel 1003-2. The greater width 1012 of needle aperture 1008 provides space for a needle to enter through substrate 310 and for stitches to be sew around tube 802 without needle puncturing tube 802. Stitches may be zigzag stiches (FIG. 8C). A width 804 of stitches 806 is adjustable to accommodate the width 808 of tube 802. Curvature of curved channel 1002 may be adjusted to accommodate the curvature of tube 802 in RF coil assembly.

Figure 11A:
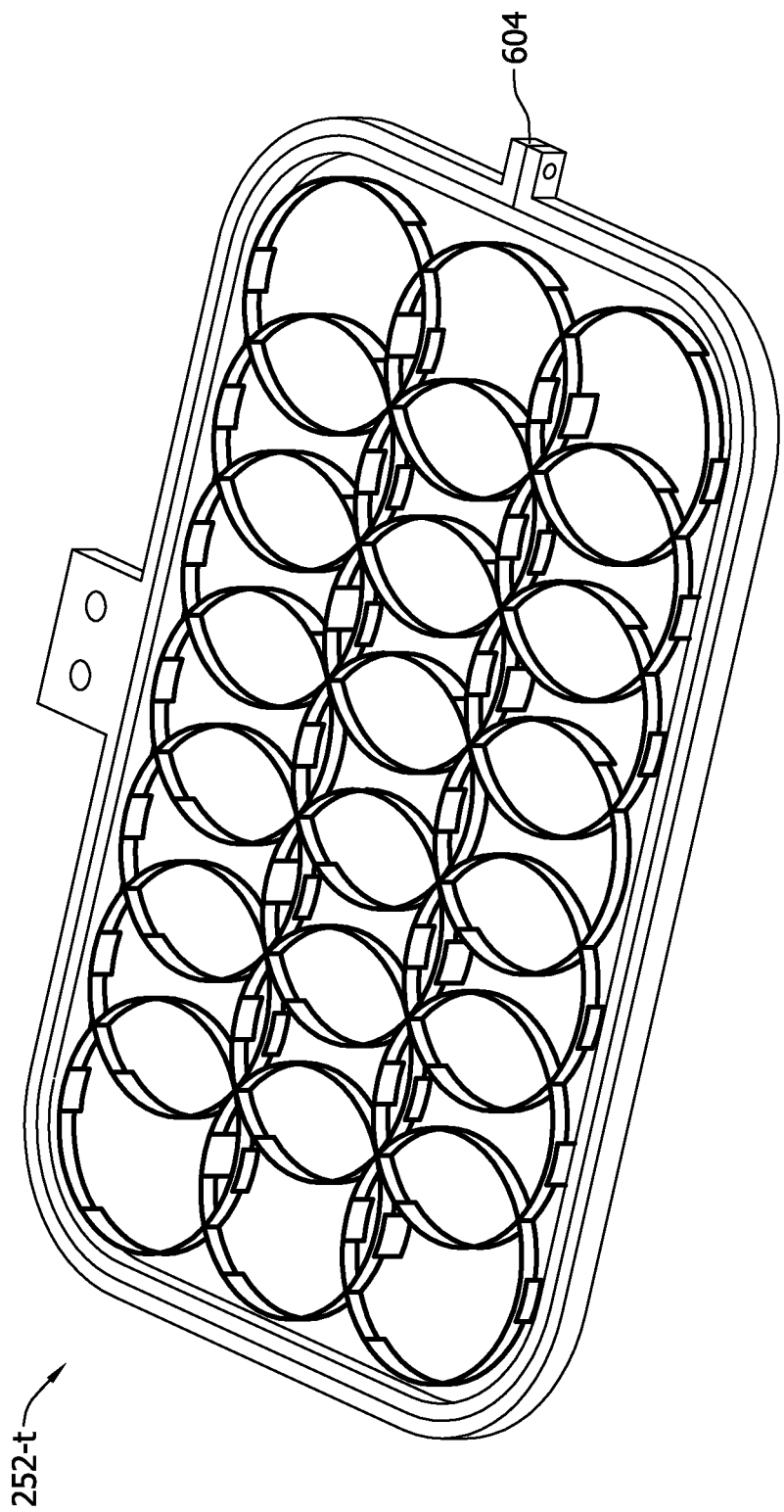
FIG. 11A is a perspective view of another example substrate holder of the sewing accessory assembly shown in FIG. 2B.
Figures 11B, 11C:
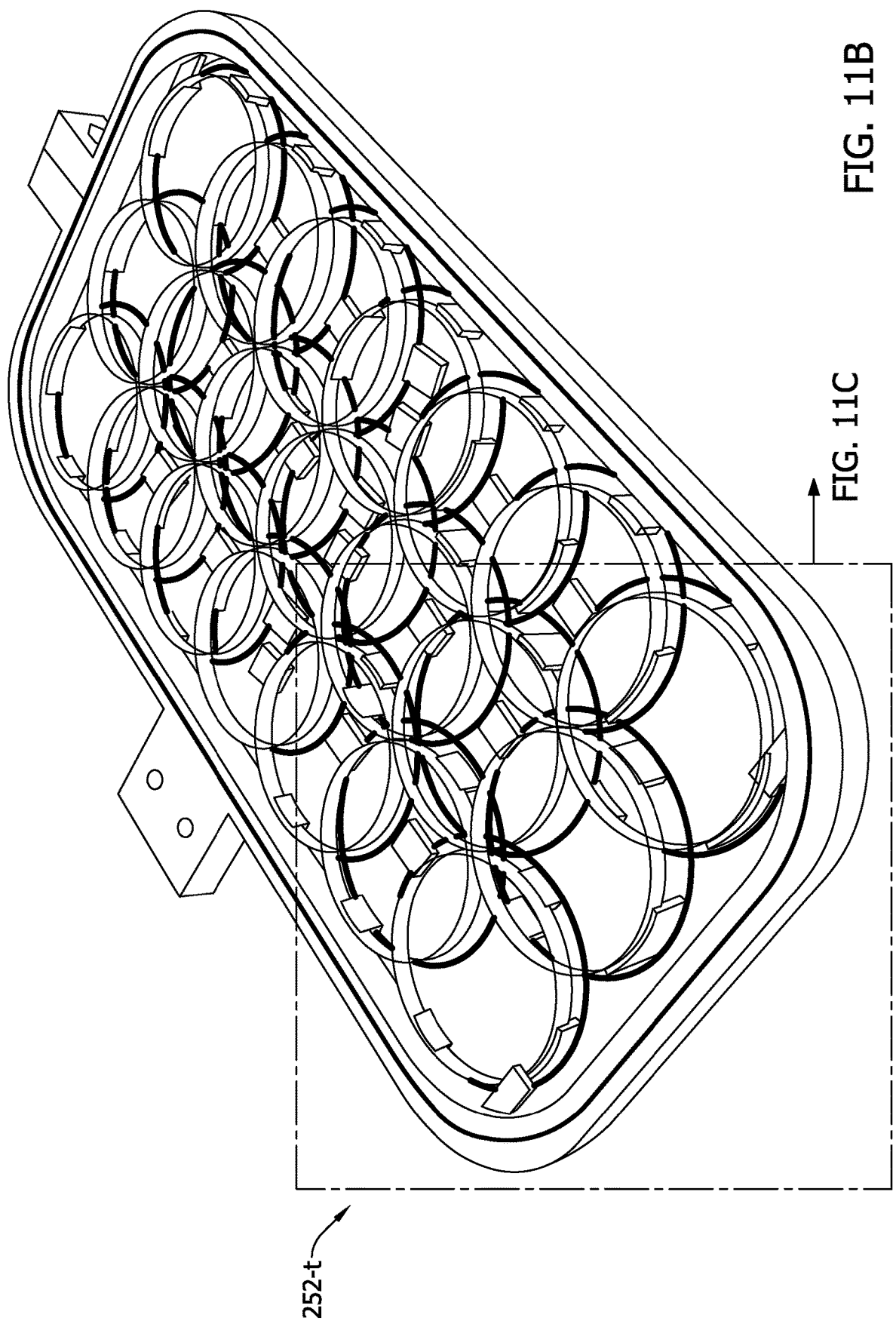
FIG. 11B is a perspective view of the substrate holder shown in FIG. 11A coupled with RF coil loops.
FIG. 11C is an enlarged view of a section of the substrate holder shown in FIG. 11B.
Figure 11C:
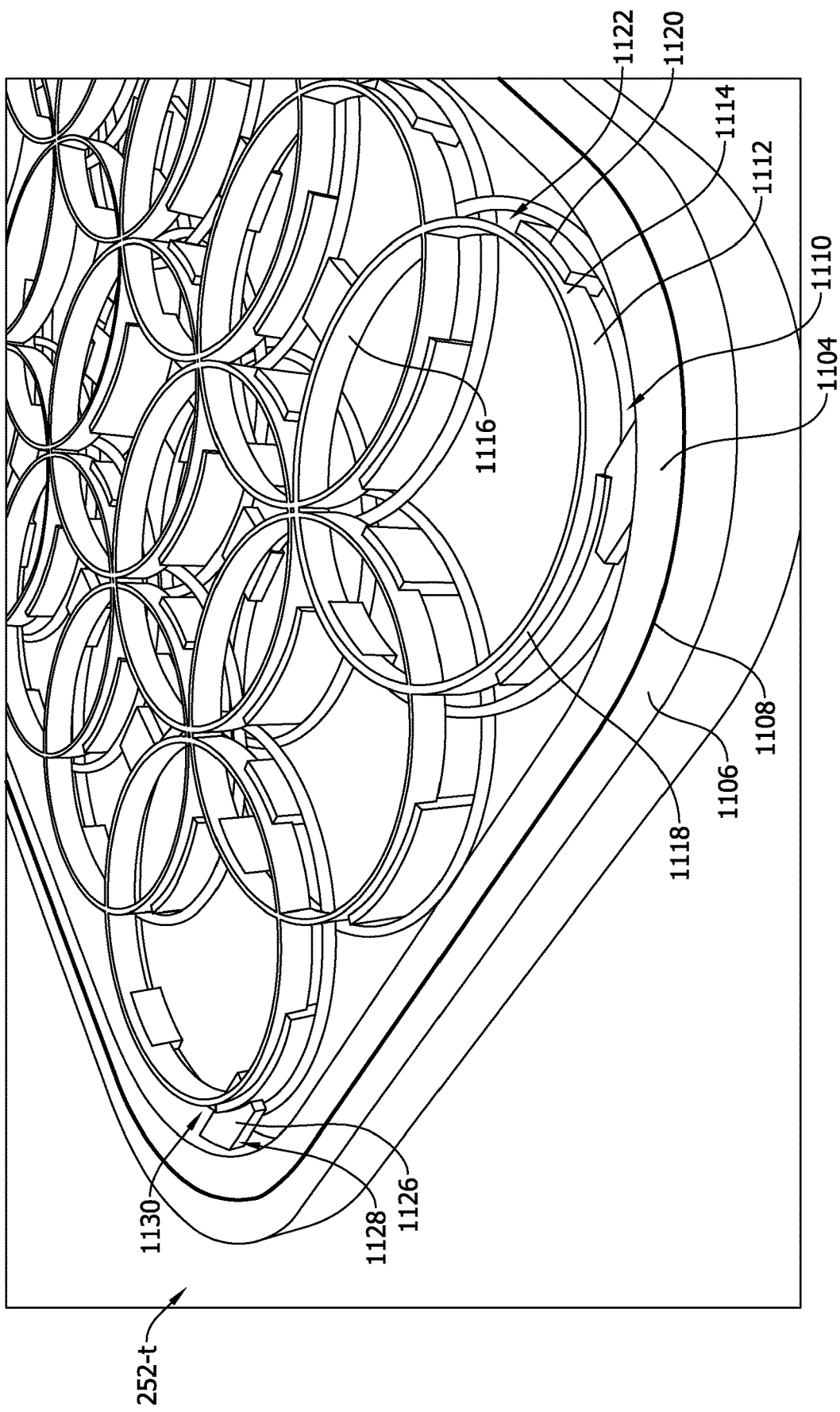
Figure 11D:
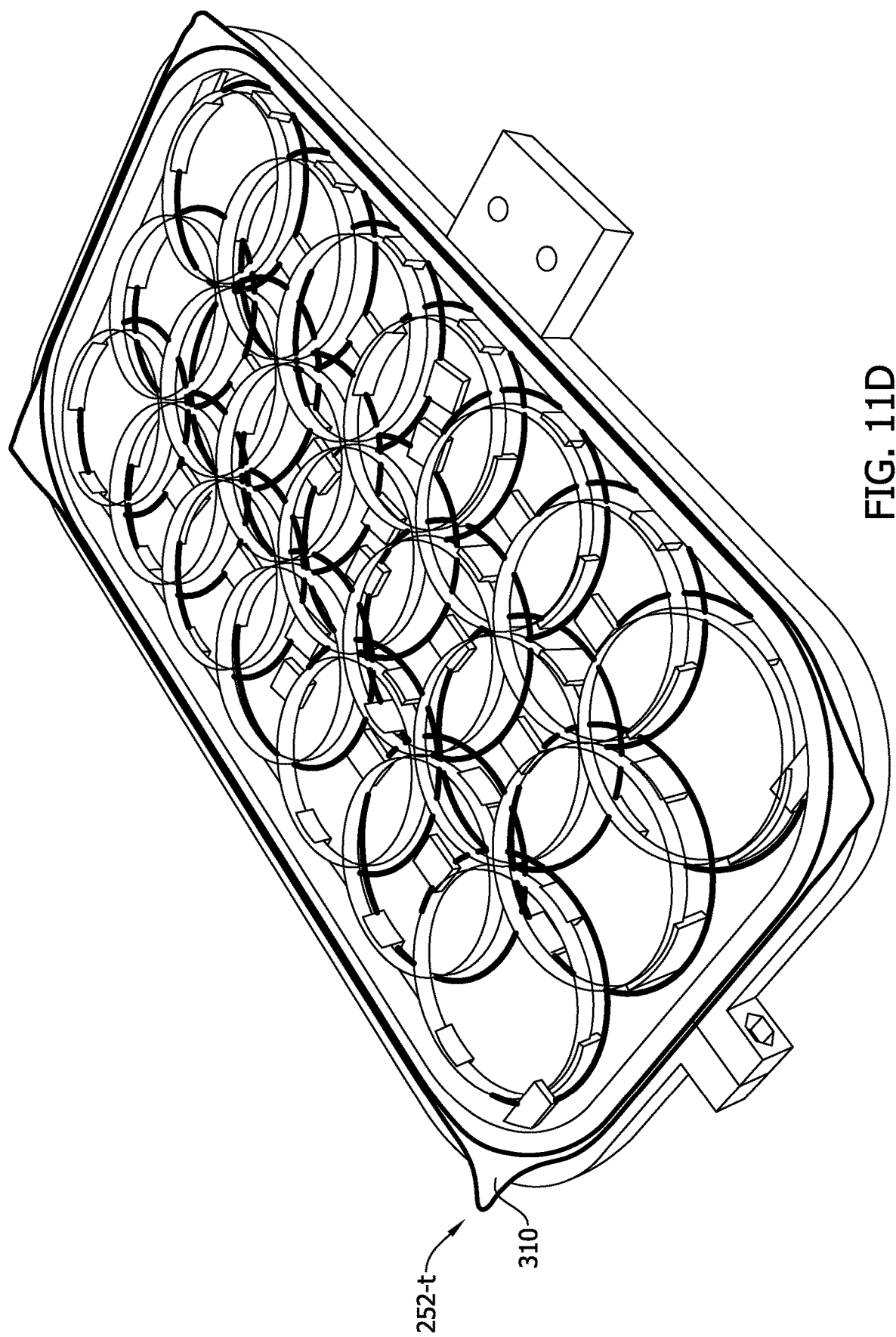
FIG. 11D is a perspective view of the substrate holder shown in FIG. 11B further coupled with a substrate.
Figure 11E:
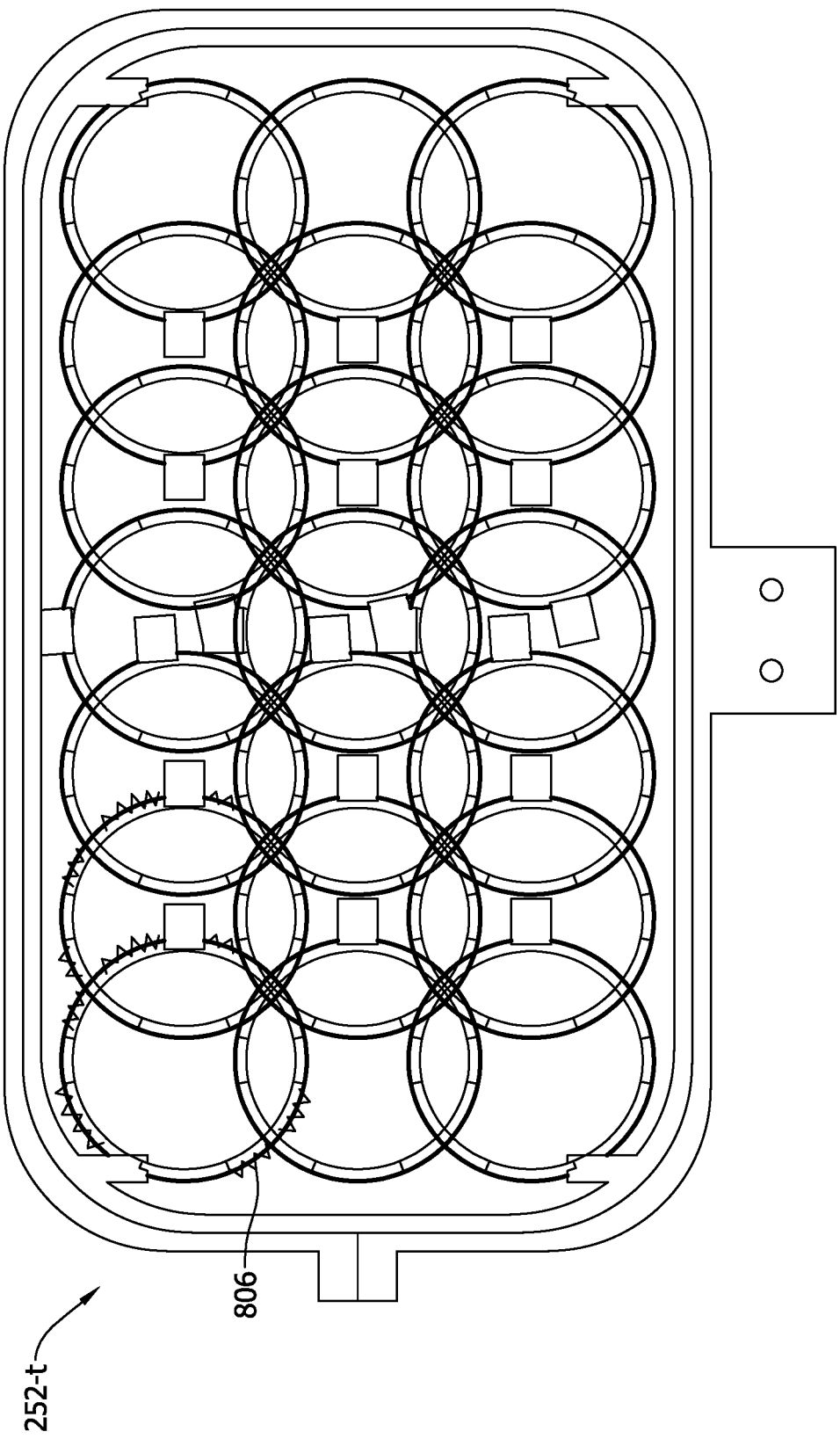
FIG. 11E is a schematic diagram illustrating RF coils are assembled using the method shown in FIG. 9.

FIGS. 11A-11F show another example substrate holder 252-*t*. FIG. 11A is a perspective view of substrate holder 252-*t*. FIG. 11B is a perspective view of substrate holder 252-*t* coupled with coil loops 201. FIG. 11C is an enlarged view of a section in FIG. 11B. FIG. 11D shows a substrate 310 is coupled in substrate holder 252-*t*. FIG. 11F shows stitches 806 are sewn on coil loops 201.

In the example embodiment, substrate holder 252-*t* includes a bracket 604 configured to couple with embroidery hoop coupler 256 of sewing machine 255. Compared to substrate holder 252 shown in FIGS. 6A and 6B, substrate holder 252-*t* does not include a bottom 611.

In the example embodiment, substrate holder 252-*t* includes an inner hoop 1104 and an outer hoop 1106. Outer hoop 1106 is sized to surround inner hoop 1104. For example, an inner dimension of outer hoop 1106 may be approximately equal to but slightly greater than an outer dimension of inner hoop 1104 such that inner hoop 1104 is positioned inside outer hoop 1106, providing a gap 1108 between inner hoop 1104 and outer hoop 1106 that is sized to receive a stretchable substrate 310 therethrough. The difference in the inner dimension of outer hoop 1106 and outer dimension of inner loop 1104 may be approximately equal to or smaller than a thickness of substrate 310 such that substrate 310 is held by inner hoop 1104 and outer hoop 1106.

In the example embodiment, substrate holder 252 further includes coil loop supports 1110 configured to receive coil loops thereon. Coil loop support 1110 includes a support body 1112 and forms a loop 1114. Loop 1114 may be circular. Coil loop support 1110 may be in other shapes, such as rectangular or polygonal, in which shapes coil loops 201 are in RF coil assembly 302. Support body 1112 includes an inner surface 1116 and an outer surface 1118 positioned opposite from inner surface 1116 (FIG. 11C). Coil loop support 1110 may include protrusions 1120 positioned on outer surface 1118. Protrusions 1120 extend outward from loop 1114 such that a gap 1122 is provided when coil loop 201 is coupled with coil loop support 1110. Gap 1122 provides space for stitches 806 to be sewn around coil loop 201. The pattern of coil loop supports 1110 is based on the pattern of coil loops 201 of RF coil assembly 302 such that when coil loops 201 are coupled with coil loop supports 1110, the layout of coil loops 201 is according to the pattern designed for RF coil assembly 302. Further, unlike embroidery hoops 602 (FIG. 6C), where the center area 616 is prone to sagging, coil loop supports 1110 provide support to stretchable substrate 310, reducing sagging from the tucking and pulling of needle 260. For example, coil loop supports 1110 provide support to stretchable substrate 310 such that areas away from inner hoop 1104 do not suffer from more sagging than areas proximate to inner hoop 1104. As a result, a former used to reduce sagging in the center area may be eliminated in fabricating liquid metal RF coil assemblies, unlike in embroidery, a stabilizer is needed for this purpose.

In the example embodiment, coil loop supports 1110 are coupled with inner hoop 1104. Coil loop supports 1110 may be coupled with inner hoop 1104 via a connector 1126. Connector 1126, coil loop supports 1110, and inner hoop 1104 may be integrally fabricated as one single piece or having only one piece. Alternatively, coil loop supports 1110 are removably coupled with inner hoop 1104. For example, inner hoop 1104 defines apertures 1128 sized to receive connector 1126 therein. In another example, coil loop supports 1110 define a slot 1130 sized to receive connector 1126. Removably couplable coil loop supports 1110 enable changes of the designs of coil loops 201 in RF coil assembly 302 by only replacing coil loop supports 1110.

In operation, coil loops 201 are coupled with coil loop supports 1110. Substrate 310 may a stretchable fabric. Substrate 310 is placed over coil loops 201. In some embodiment, a former (not shown) is placed further over substrate 310 configured to reduce sagging of substrate 310 or deformation of substrate 310 during sewing. Outer hoop 1106 is then placed over substrate 310 and/or former such that sides of substrate 310 and/or former are held between inner hoop 1104 and outer hooper 1106. The assembled substrate holder 252 is flipped over such that coil loops are facing an operator during sewing. The assembled substrate holder 252 is coupled with embroidery hoop coupler 256 of sewing machine 255. Stitches 806 may be applied at desired locations on coil loops 201.

In the example embodiment, coupling electronics portions 203 may have been coupled with coil loops 201 before sewing. Alternatively, coupling electronics portions 203 are coupled with coil loops after sewing.

Figure 12:
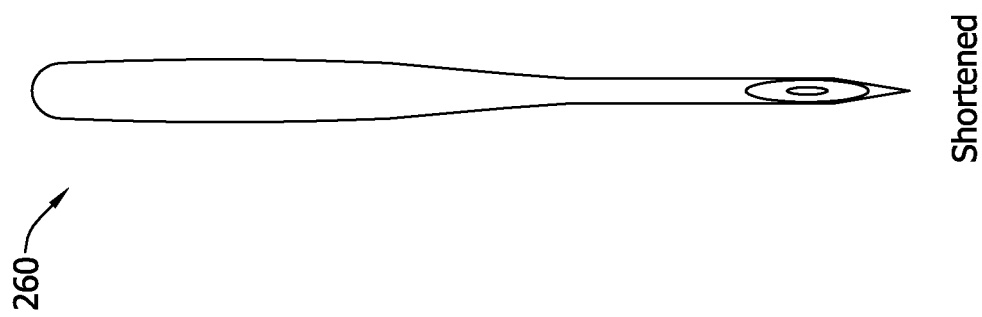
FIG. 12 shows one more example needle of the sewing accessory assembly shown in FIG. 2B.

FIG. 12 shows one more example needle 260. In the example embodiment, needle 260 is shorter than standard sewing needles 701 of a sewing machine 255. Needle 260 having a reduced length is advantageous in sewing coil loops 201 with a stretchable substrate 310 and/or a former, which may have a thickness greater than the thickness of fabrics or components used in conventional sewing.

Referring back to FIG. 9, in the example embodiment, method 400-*t* further includes coupling 901 an RF coil loop filled with liquid metal on one of the one or more coil loop support. Method 400 further includes assembling 902 a stretchable substrate with a substrate holder by securing the stretchable substrate between the inner hoop and outer hoop. In some embodiments, a former is placed over the stretchable substrate to further reduce deformation or sagging of the stretchable substrate during sewing from the pulling and tucking of the needle, due to limited tension provided by the inner hoop and the outer hoop. Method 400 further includes coupling 904 the assembled substrate holder with a sewing machine. For example, assembled substrate holder 252 is coupled with sewing machine 255 by coupling bracket 604 with embroidery hoop coupler 256 of sewing machine 255. The height of a presser foot or the height of a needle of sewing machine 255 may be adjusted based on the thickness of coil loop 201, substrate 310, and/or the former. An RF coil assembly is assembled 906 by sewing stitches to attach the RF coil loops of the RF coil assembly 302 with the stretchable substrate. If a former is used, former is removed from RF coil assembly 302. The former may be water soluble such that the former is removed by being dissolved in water. Example material of a former is polyvinyl alcohol (PVA). The former does not produce a detectable level of proton MR signals. The performance of RF coil assemblies therefore is not affected even if the former is not completely removed. Coupling electronics portion 203 may be coupled with coil loops 201 after the removal of the former.

At least one technical effect of the systems and methods described herein includes (a) automized and customized methods of fabricating liquid metal RF coil assemblies using a sewing machine; (b) presser feet of a sewing machine for fabricating liquid metal RF coil assemblies; (c) substrate holders configured to hold substrate of RF coils and to couple with a sewing machine like an embroidery hoop; and (d) needles for fabricating liquid metal RF coil assemblies.

Example embodiments of assemblies, systems, and methods of fabricating liquid metal RF coil assemblies are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of fabricating a liquid metal radio-frequency (RF) coil assembly of a magnetic resonance (MR) system using a sewing machine, comprising:
    providing a sewing accessory assembly, the sewing accessory assembly including:
        a substrate holder; and
        a presser foot;
    attaching the presser foot with a sewing machine;
    positioning the substrate holder containing a first substrate underneath a needle arm of the sewing machine;
    carving a pattern of grooves on a surface of the first substrate using the presser foot by operating the sewing machine;
    forming RF coil loops by depositing liquid metal in the grooves; and
    applying a second substrate over the RF coil loops.

2. The method of claim 1, wherein the presser foot further includes:
    a foot body including a top surface and a bottom surface opposite the top surface; and
    a wedge positioned on the bottom surface and extending away from the foot body.

3. The method of claim 2, wherein carving a pattern further comprises:
    attaching the presser foot to the sewing machine such that the wedge faces the substrate holder.

4. The method of claim 1, wherein the sewing accessory assembly further includes a needle, the needle does not include an eye, and carving a pattern further comprises:
    attaching the needle to the sewing machine; and
    producing apertures in the first substrate by the needle.

5. The method of claim 4, wherein the needle includes a needle body and a needle tip extending from the needle body and tapered from the needle body, wherein producing apertures further comprises:
    reducing sizes of the apertures by:
        producing the apertures in the first substrate by the needle.

6. The method of claim 4, wherein the needle includes a needle body, and a needle tip extending from the needle body and defining a blunt end, wherein producing apertures further comprises:
    producing the apertures in the first substrate by the blunt end.

7. The method of claim 1, wherein carving a pattern further comprises:
    customizing the pattern of grooves;
    loading the customized pattern to the sewing machine; and
    operating the sewing machine such that the presser foot moves according to the customized pattern.

8. A method of fabricating a liquid metal radio-frequency (RF) coil assembly of a magnetic resonance (MR) system using a sewing machine, comprising:
    providing a sewing accessory assembly, the sewing accessory assembly including a substrate holder, the substrate holder including:
        an inner hoop;
        one or more coil loop supports configured to be coupled with the inner hoop and be positioned within the inner hoop; and
        an outer hoop;
    coupling an RF coil loop filled with liquid metal on one of the one or more coil loop supports;
    assembling a stretchable substrate with the substrate holder by:
        securing the stretchable substrate between the inner hoop and the outer hoop;
    coupling the assembled substrate holder with a sewing machine; and
    assembling a liquid metal RF coil assembly by:
        sewing stitches to attach the RF coil loop with the stretchable substrate.

9. The method of claim 8, wherein the sewing accessory assembly further includes a presser foot, the presser foot defines a channel, wherein:

sewing stitches further comprises positioning the RF coil loop along the channel during sewing.

10. The method of claim 9, wherein the channel is curved.

11. The method of claim 8, wherein assembling a stretchable substrate further comprises:
assembling a former and the stretchable substrate with the substrate holder by:
securing the former and the stretchable substrate between the inner hoop and the outer hoop.

12. The method of claim 11, wherein the former is soluble in water, the method further comprising:
removing the former from the liquid metal RF coil assembly by:
dissolving the former using water.

13. A sewing accessory assembly of a sewing machine for fabricating a radio-frequency (RF) coil assembly of a magnetic resonance (MR) system, comprising:
a presser foot, the presser foot comprising:
a foot body including a top surface and a bottom surface opposite the top surface; and
a wedge positioned on the bottom surface and extending away from the foot body; and
a substrate holder configured to be coupled with an embroidery hoop coupler of a sewing machine.

14. The sewing accessory assembly of claim 13, wherein the substrate holder further comprises:
edges; and
a bottom surface extending between the edges,
where the edges and the bottom surface define a receptacle sized to receive a substrate.

15. The sewing accessory assembly of claim 13, further comprising:
a needle not including an eye.

16. The sewing accessory assembly of claim 15, wherein the needle comprises:
a needle body; and
a needle tip extending from the needle body and tapered from the needle body.

17. The sewing accessory assembly of claim 15, wherein the needle comprises:
a needle body; and
a needle tip extending from the needle body and defining a blunt end.

18. The sewing accessory assembly of claim 13, wherein the substrate holder comprises:
an inner hoop;
one or more coil loop supports configured to be coupled with the inner hoop and be positioned within the inner hoop; and
an outer hoop sized to surround the inner hoop.

19. The sewing accessory assembly of claim 13, wherein the one or more coil loop supports comprise a plurality of coil loop supports, and at least two of the plurality of coil loop supports overlap with one another.

20. The sewing accessory assembly of claim 13, wherein at least one of the one or more coil loop supports includes:
a support body defining a loop and having an inner surface and outer surface opposite the inner surface; and
protrusions positioned on the outer surface.

* * * * *